(12) United States Patent
Melvin et al.

(10) Patent No.: US 11,767,516 B2
(45) Date of Patent: Sep. 26, 2023

(54) METHODS AND COMPOSITIONS FOR THIOL-ACRYLATE BASED MATERTALS FOR 3D CELL CULTURING IN A MICROFLUIDIC DEVICE

(71) Applicant: Board of Supervisors of Louisiana State University and Agricultural and Mechanical College, Baton Rouge, LA (US)

(72) Inventors: Adam Melvin, Baton Rouge, LA (US); John Pojman, Baton Rouge, LA (US); Anowar Khan, Baton Rouge, LA (US)

(73) Assignee: Board of Supervisors of Louisiana State University, Baton Rouge, LA (US)

( * ) Notice: Subject to any disclaimer, the term of this patent is extended or adjusted under 35 U.S.C. 154(b) by 225 days.

(21) Appl. No.: 17/116,289

(22) Filed: Dec. 9, 2020

(65) Prior Publication Data

US 2021/0180028 A1    Jun. 17, 2021

Related U.S. Application Data

(60) Provisional application No. 62/946,667, filed on Dec. 11, 2019.

(51) Int. Cl.
*C08G 75/04* (2016.01)
*C12N 5/09* (2010.01)
*C12M 3/06* (2006.01)
*C12N 5/00* (2006.01)

(52) U.S. Cl.
CPC ........... *C12N 5/0693* (2013.01); *C08G 75/04* (2013.01); *C12M 23/16* (2013.01); *C12N 5/0062* (2013.01); *C12N 2500/05* (2013.01); *C12N 2500/34* (2013.01); *C12N 2513/00* (2013.01); *C12N 2533/30* (2013.01)

(58) Field of Classification Search
None
See application file for complete search history.

(56) References Cited

U.S. PATENT DOCUMENTS

| | | | |
|---|---|---|---|
| 2013/0142781 A1* | 6/2013 | Langer | A61L 24/0015 514/17.7 |
| 2013/0149318 A1* | 6/2013 | Reynolds | A61K 9/0085 514/169 |

(Continued)

OTHER PUBLICATIONS

Mancha Sánchez, Enrique, et al. "Hydrogels for bioprinting: a systematic review of hydrogels synthesis, bioprinting parameters, and bioprinted structures behavior." Frontiers in Bioengineering and Biotechnology 8 (2020): 776. (Year: 2020).*

(Continued)

*Primary Examiner* — Robert S Loewe
(74) *Attorney, Agent, or Firm* — THOMAS|HORSTEMEYER, LLP

(57) ABSTRACT

Provided are thiol-acrylate hydrogels and tunable cell culture materials including thiol-acrylate hydrogels, and methods of making thereof. Also provided are systems for forming three-dimensional cell culture scaffolds including the materials, and methods of culturing cells, including cancer cells, using thiol-acrylate hydrogels and tunable cell culture materials. The materials herein can be used in microfluidic droplet-generating devices.

18 Claims, 15 Drawing Sheets

(56) References Cited

U.S. PATENT DOCUMENTS

| | | | |
|---|---|---|---|
| 2019/0247546 A1* | 8/2019 | Papadimitriou | A61L 27/52 |
| 2020/0009277 A1* | 1/2020 | Showalter | A61K 47/34 |

OTHER PUBLICATIONS

Uto K, Tsui JH, DeForest CA, Kim DH. Dynamically Tunable Cell Culture Platforms for Tissue Engineering and Mechanobiology. Prog Polym Sci. Feb. 2017;65:53-82. doi: 10.1016/j.progpolymsci. 2016.09.004. Epub Sep. 17, 2016. Erratum in: Prog Polym Sci. Jul. 2017;70:92. PMID: 28522885; PMCID: PMC5432044. (Year: 2016).*

Kersker, Nathan Daniel. High-Throughput Assessment of a Novel, Thiol-Acrylate Hydrogel for Tumor Spheroid Synthesis in a Microfluidic Device. Louisiana State University and Agricultural & Mechanical College, 2018. (Year: 2018).*

Phosphate Buffered Saline data sheet, 2 pages, 2006. (Year: 2006).*

Bissell, M. J.; LaBarge, M. A., Context, tissue plasticity, and cancer. Cancer Cell 2005, 7 (1), 17-23.

Nath, S.; Devi, G. R., Three-dimensional culture systems in cancer research: Focus on tumor spheroid model. Pharmacology & Therapeutics 2016, 163, 94-108.

Jang, M.; Yang, S.; Kim, P. J. B. J., Microdroplet-based cell culture models and their application. Biochip Journal 2016, 10(4), 310-317.

Sabhachandani, P.; Motwani, V.; Cohen, N.; Sarkar, S.; Torchilin, V.; Konry, T., Generation and functional assessment of 3D multicellular spheroids in droplet based microfluidics platform. Lab on a Chip 2016, 16 (3), 497-505.

Wang, Y.; Wang, J., Mixed hydrogel bead-based tumor spheroid formation and anticancer drug testing. Analyst 2014, 139 (10), 2449-2458.

Li, Y.; Kumacheva, E., Hydrogel microenvironments for cancer spheroid growth and drug screening. Science Advances 2018, 4 (4), eaas8998.

Mloshksayan, K.; Kashaninejad, N.; Warkiani, M. E.; Lock, J. G.; Moghadas, H.; Firoozabadi, B.; Saidi, M. S.; Nguyen, N.-T., Spheroids-on-a-chip: Recent advances and design considerations in microfluidic platforms for spheroid formation and culture. Sensors and Actuators B: Chemical 2018, 263, 151-176.

Drury, J. L.; Mooney, D. J., Hydrogels for tissue engineering: scaffold design variables and applications. Biomaterials 2003, 24 (24), 4337-4351.

Buwalda, S. J.; Dijkstra, P. J.; Feijen, J., In Situ Forming Poly(ethylene glycol)-Poly(L-lactide) Hydrogels via Michael Addition: Mechanical Properties, Degradation, and Protein Release. Macromolecular Chemistry and Physics 2012, 213 (7), 766-775.

Jin, R.; Hiemstra, C.; Zhong, Z.; Feijen, J., Enzyme-mediated fast in situ formation of hydrogels from dextran-tyramine conjugates. Biomaterials 2007, 28 (18), 2791-2800.

Sakai, S.; Hirose, K.; Taguchi, K.; Ogushi, Y.; Kawakami, K., An injectable, in situ enzymatically gellable, gelatin derivative for drug delivery and tissue engineering. Biomaterials 2009, 30 (20), 3371-3377.

Gu, L.; Mooney, D. J., Biomaterials and emerging anticancer therapeutics: engineering the microenvironment. Nature Reviews Cancer 2015, 16, 56.

Wang, J.; He, H.; Cooper, R. C.; Yang, H., In Situ-Forming Polyamidoamine Dendrimer Hydrogels with Tunable Properties Prepared via Aza-Michael Addition Reaction. ACS Applied Materials & Interfaces 2017, 9 (12), 10494-10503.

Sabnis, A.; Rahimi, M.; Chapman, C.; Nguyen, K. T., Cytocompatibility studies of an in situ photopolymerized thermoresponsive hydrogel nanoparticle system using human aortic smooth muscle cells. Journal of Biomedical Materials Research 2009, 91A (1), 52-59.

Cuchiara, M. P.; Allen, A. C. B.; Chen, T. M.; Miller, J. S.; West, J. L., Multilayer microfluidic PEGDA hydrogels. Biomaterials 2010, 31 (21), 5491-5497.

Cavallo, A.; Madaghiele, M.; Masullo, U.; Lionetto, M. G.; Sannino, A., Photo-crosslinked poly(ethylene glycol) diacrylate (PEGDA) hydrogels from low molecular weight prepolymer: Swelling and permeation studies. Journal of Applied Polymer Science 2017, 134 (2) 44380.

Huynh, C. T.; Liu, F.; Cheng, Y.; Coughlin, K. A.; Alsberg, E., Thiol-Epoxy "Click" Chemistry to Engineer Cytocompatible PEG-Based Hydrogel for siRNA-Mediated Osteogenesis of hMSCs. ACS Applied Materials & Interfaces 2018, 10 (31), 25936-25942.

McMahon, S.; Kennedy, R.; Duffy, P.; Vasquez, J. M.; Wall, J. G.; Tai, H.; Wang, W., Poly(ethylene glycol)-Based Hyperbranched Polymer from RAFT and Its Application as a Silver-Sulfadiazine-Loaded Antibacterial Hydrogel in Wound Care. ACS Applied Materials & Interfaces 2016, 8 (40), 26648-26656.

Jee, E.; Bánsági, T.; Taylor, A. F.; Pojman, J. A., Temporal Control of Gelation and Polymerization Fronts Driven by an Autocatalytic Enzyme Reaction. Angewandte Chemie 2016, 128 55 (6), 2127-2131.

Zhang, W.; Li, C.; Baguley, B. C.; Zhou, F.; Zhou, W.; Shaw, J. P.; Wang, Z.; Wu, Z.; Liu, J., Optimization of the formation of embedded multicellular spheroids of MCF-7 cells: How to reliably produce a biomimetic 3D model. Analytical Biochemistry 2016, 515, 47-54.

Sant, S.; Johnston, P. A., The production of 3D tumor spheroids for cancer drug discovery. Drug Discovery Today: Technologies 2017, 23, 27-36.

Kharkar, P. M.; Kloxin, A. M.; Kiick, K. L., Dually degradable click hydrogels for controlled degradation and protein release. Journal of Materials Chemistry B 2014, 2 (34), 5511-5521.

Caliari, S. R.; Burdick, J. A., A practical guide to hydrogels for cell culture. Nature Methods 2016,13, 405.

Ray, E.; Bunton, P.; Pojman, J. A., Determination of the diffusion coefficient between corn syrup and distilled water using a digital camera. American Journal of Physics 2007, 75 (10), 903-906.

Antrim, D.; Bunton, P.; Lewis, L. L.; Zoltowski, B. D.; Pojman, J. A., Measuring the Mutual Diffusion Coefficient for Dodecyl Acrylate in Low Molecular Weight Poly(dodecyl acrylate) with Laser Line Deflection (Wiener's Method) and the Fluorescence of Pyrene. The Journal of Physical Chemistry B 2005, 109 (23), 11842-11849.

Doll, K. M.; Vermillion, K. E.; Fanta, G. F.; Liu, Z., Diffusion coefficients of water in biobased hydrogel polymer matrices by nuclear magnetic resonance imaging Journal of Applied Polymer Science 2012, 125 (S2), E580-E585.

Khelfallah, N. S.; Decher, G.; Mésini, P. J. J. B., Design, synthesis, and degradation studies of new enzymatically erodible Poly(hydroxyethyl methacrylate)/poly(ethylene oxide) hydrogels. Biointerphases 2007, 2 (4), 131-135.

Li, X.; Tsutsui, Y.; Matsunaga, T.; Shibayama, M.; Chung, U.-i.; Sakai, T., Precise Control and Prediction of Hydrogel Degradation Behavior. Macromolecules 2011, 44 (9), 3567-3571.

Fu, Y.; Xu, K.; Zheng, X.; Giacomin, A. J.; Mix, A. W.; Kao, W. J., 3D cell entrapment in crosslinked thiolated gelatin-poly(ethylene glycol) diacrylate hydrogels. Biomaterials 2012, 33 (1), 48-58.

Bader, R. A.; Rochefort, W. E., Rheological characterization of photopolymerized poly(vinyl alcohol) hydrogels for potential use in nucleus pulposus replacement. Journal of Biomedical Materials Research 2008, 86A (2), 494-501.

M. Vaithiyanathan, N. Safa, and A. T. Melvin, FluoroCellTrack: An Algorithm for Automated Analysis of High-throughput Droplet Microfluidic Data. Plos One Under Review 20198 14(5)c e0125337.

Chan, J. W.; Hoyle, C. E.; Lowe, A. B.; Bowman, M., Nucleophile-Initiated Thiol-Michael Reactions: Effect of Organocatalyst, Thiol, and Ene. Macromolecules 2010, 43 (15), 6381-6388. Macromolecules 2010, 43 (15), 6381-6388.

Liang, Y.; Coffin, M. V.; Manceva, S. D.; Chichester, J. A.; Jones, R. M.; Kiick, K. L., Controlled release of an anthrax toxin-neutralizing antibody from hydrolytically degradable polyethylene glycol hydrogels. Journal of Biomedical Materials Research 2016, 104 (1), 113-123.
Price, J. T.; Tiganis, T.; Agarwal, A.; Djakiew, D.; Thompson, E. W., Epidermal Growth Factor Promotes MDA-MB-231 Breast Cancer Cell Migration through a Phosphatidylinositol 3'-Kinase and Phospholipase C-dependent Mechanism. Cancer Research 1999, 59 (21), 5475-5478.

(56) References Cited

OTHER PUBLICATIONS

Del Angel-Mosqueda, C.; Gutiérrez-Puente, Y.; López-Lozano, A. P.; Romero-Zavaleta, R. E.; Mendiola-Jiménez, A.; Medina-De la Garza, C. E.; Márquez-M, M.; De la Garza-Ramos, M. A. J. H.; Medicine, F., Epidermal growth factor enhances osteogenic differentiation of dental pulp stem cells in vitro. Head and Face Medicine 2015, 11 (1), 29.

McMurtrey, R. J. J., M. R., Analytic Models of Oxygen and Nutrient Diffusion, Metabolism Dynamics, and Architecture Optimization in Three-Dimensional Tissue Constructs with Applications and Insights in Cerebral Organoids. Tissue Engineering Part C 2016, 22 (3), 221-249.

Wang, Y.; Ding, S.; Gong, M.; Xu, S.; Xu, W.; Zhang, C., Diffusion characteristics of agarose hydrogel used in diffusive gradients in thin films for measurements of cations and anions. Analytica Chimica Acta 2016, 945, 47-56.

Figueiredo, L.; Pace, R.; D'Arros, C.; Réthoré, G.; Guicheux, J.; Le Visage, C.; Weiss, P., Assessing glucose and oxygen diffusion in hydrogels for the rational design of 3D stem cell scaffolds in regenerative medicine. Journal of Tissue Engineering and Regenerative Medicine 2018, 12 (5), 1238-1246.

Osidak, E. O.; Osidak, M. S.; Akhmanova, M. A.; Domogatskii, S. P. J. R. J. o. G. C., Collagen—A biomaterial for delivery of growth factors and tissue regeneration. Russian Journal of General Chemistry 2014, 84 (2), 368-378.

Betz, M.; Hörmansperger, J.; Fuchs, T.; Kulozik, U., Swelling behaviour, charge and mesh size of thermal protein hydrogels as influenced by pH during gelation. Soft Matter 2012, 8 (8), 2477-2485.

Hajova, H.; Chmelar, J.; Nistor, A.; Gregor, T.; Kosek, J., Experimental Study of Sorption and Diffusion of n-Pentane in Polystyrene Journal of Chemical & Engineering Data 2013, 58 (4), 851-865.

Xu, K.; Fu, Y.; Chung, W.; Zheng, X.; Cui, Y.; Hsu, I. C.; Kao, W. J., Thiol-ene-based biological/synthetic hybrid biomatrix for 3-D living cell culture Acta Biomaterialia 2012, 8 (7), 2504-2516.

Yeung, T.; Georges, P. C.; Flanagan, L. A.; Marg, B.; Ortiz, M.; Funaki, M.; Zahir, N.; Ming, W.; Weaver, V.; Janmey, P. A., Effects of substrate stiffness on cell morphology, cytoskeletal structure, and adhesion. Cytoskeleton 2005, 60(1), 24-34.

Zustiak, S. P.; Leach, J. B., Hydrolytically Degradable Poly(Ethylene Glycol) Hydrogel Scaffolds with Tunable Degradation and Mechanical Properties. Biomacromolecules 2010, 11 (5), 1348-1357.

Totaro, N. P.; Murphy, Z. D.; Burcham, A. E.; King, C. T.; Scherr, T. F.; Bounds, C. O.; Dasa, V.; Pojman, J. A.; Hayes, D. J., In vitro evaluation of thermal frontally polymerized thiol-ene composite as bone augments. Journal of Biomedical Materials Research 2016, 104 (6), 1152-1160.

Rodriguez, E. J.; Marcos, B.; Huneault, M. A., Hydrolysis of polylactide in aqueous media. Journal of Applied Polymer Science 2016, 133 (44) 44152.

Tilghman, R. W.; Cowan, C. R.; Mih, J. D.; Koryakina, Y.; Gioeli, D.; Slack-Davis, J. K.; Blackman, B. R.; Tschumperlin, D. J.; Parsons, J. T., Matrix Rigidity Regulates Cancer Cell Growth and Cellular Phenotype. Plos One 2010, 5 (9), e12905.

Joyce, M. H.; Lu, C.; James, E. R.; Hegab, R.; Allen, S. C.; Suggs, L. J.; Brock, A., Phenotypic Basis for Matrix Stiffness-Dependent Chemoresistance of Breast Cancer Cells to Doxorubicin. Frontiers in Oncology 2018, 8 (337).

Nguyen, M. K.; McMillan, A.; Huynh, C. T.; Schapira, D. S.; Alsberg, E., Photocrosslinkable, biodegradable hydrogels with controlled cell adhesivity for prolonged siRNA delivery to hMSCs to enhance their osteogenic differentiation. Journal of Materials Chemistry B 2017, 5 (3), 485-495.

Nguyen, M. K.; Jeon, O.; Krebs, M. D.; Schapira, D.; Alsberg, E., Sustained localized presentation of RNA interfering molecules from in situ forming hydrogels to guide stem cell osteogenic differentiation. Biomaterials 2014, 35 (24), 6278-6286.

\* cited by examiner

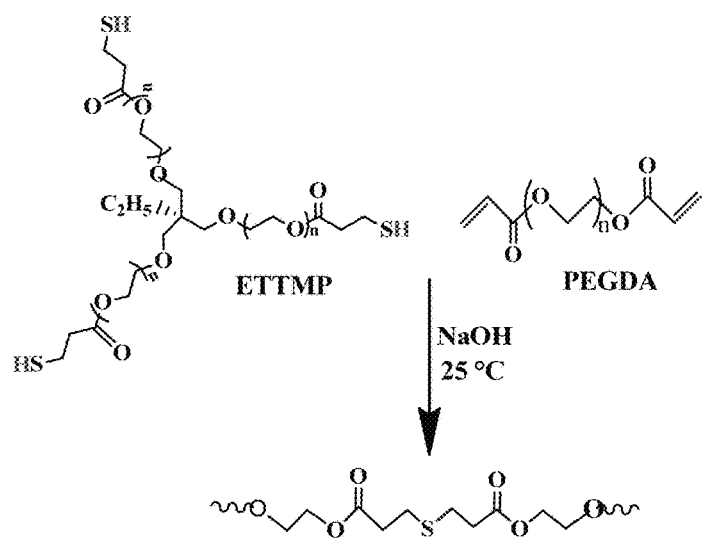
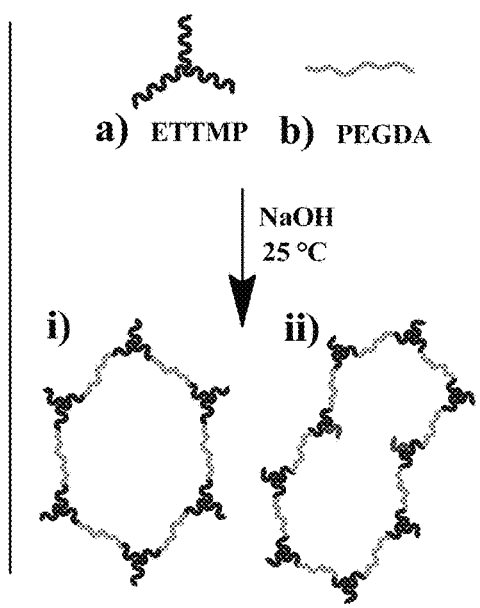
Fig. 1A        Fig. 1B
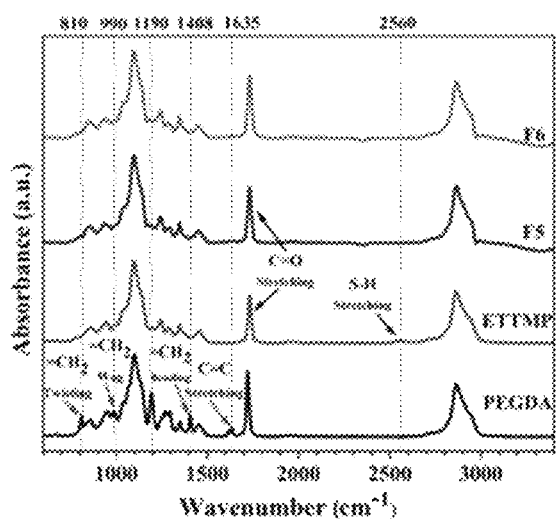
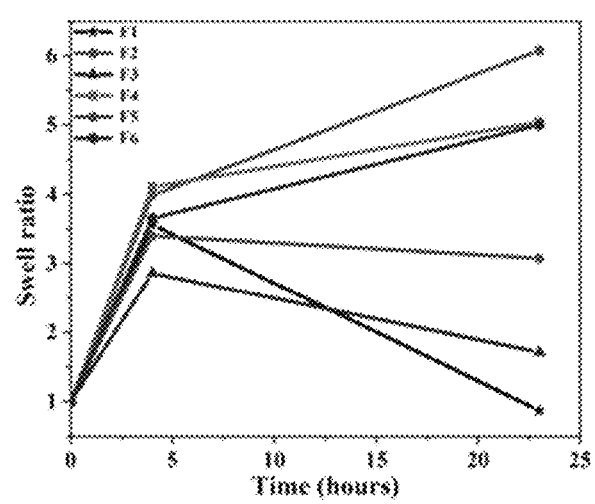
Fig. 2A        Fig. 2B

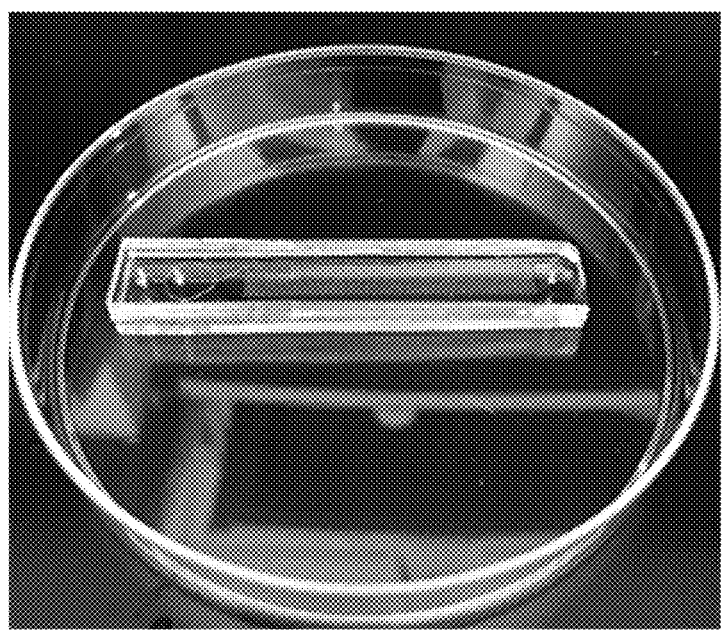
Fig. 15
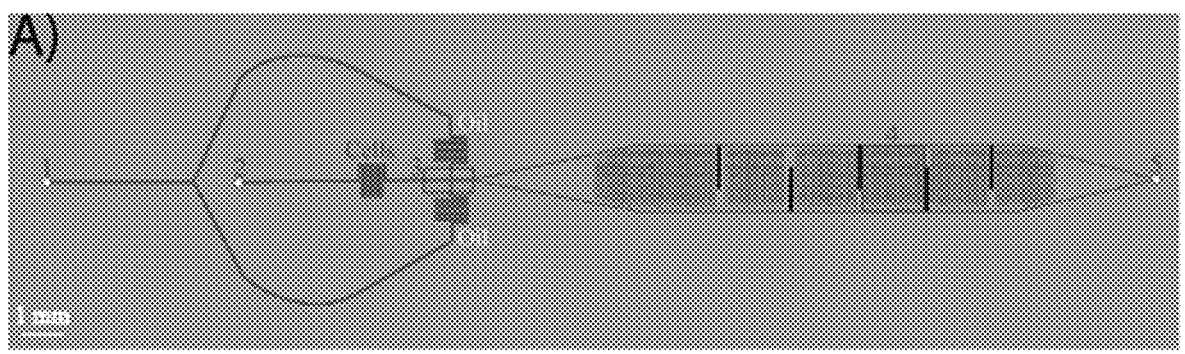
Fig. 16A
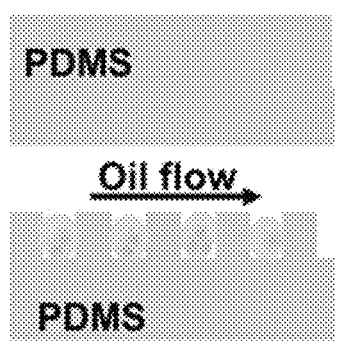 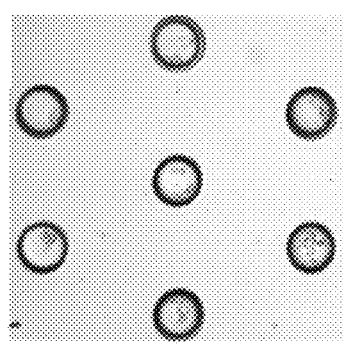 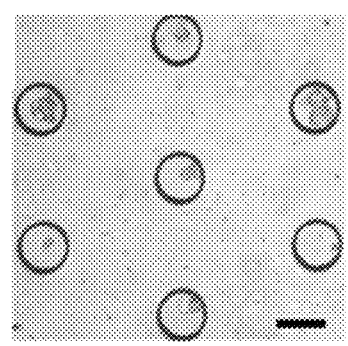
Fig. 16B                Fig. 16C                Fig. 16D

METHODS AND COMPOSITIONS FOR THIOL-ACRYLATE BASED MATERIALS FOR 3D CELL CULTURING IN A MICROFLUIDIC DEVICE

CROSS-REFERENCE TO RELATED APPLICATIONS

This application claims the benefit of and priority to U.S. Provisional Application Ser. No. 62/946,667, having the title "methods and compositions for Thiol-Acrylate Based Materials for 3D cell culturing in a microfluidic device", filed on Dec. 11, 2019, the disclosure of which is incorporated herein by reference in its entirety.

STATEMENT REGARDING FEDERALLY SPONSORED RESEARCH OR DEVELOPMENT

This invention was made with U.S. Government support under grant number CBET 1511653, awarded by The National Science Foundation. The U.S. government has certain rights in the invention.

BACKGROUND

Two-dimensional (2D) cell culturing is the most common approach for cell-based research, despite evidence of variant gene expression, differences in cell-to-cell communication, a lack of accountability for the spatial restriction of cells, and an inability to replicate mass transfer limitations including the existence of extracellular chemical gradients. In the case of cancer, tumor cells grown in a three-dimensional (3D) environment have been shown to better replicate in vivo conditions including cell-to-cell interactions, metabolite and drug transfer, and population heterogeneity—all characteristics lacking in modern 2D culturing approaches. Moreover, recent studies have shown increased drug resistance in cancer cells cultured in a 3D environment compared to cells cultured in 2D when exposed to common anti-cancer compounds. The tumor microenvironment is a complex system consisting of multiple types of cells (e.g., cancer, stromal, and immune cells) surrounded by extracellular matrix (ECM) deposition between the cells to facilitate cell-to-cell interaction, allow for the creating of extracellular chemical gradients, and provide a scaffold to support cellular growth. The ECM provides mechanical and chemical properties to proliferative cells; these properties can modulate cellular behavior. Such properties include stiffness, durability, temperature control, protein content, and the potential for degradation. Currently, the best approach for the 3D culture of cancer cells involves the growth and study of spheroids—three-dimensional, well-rounded cell aggregations that consist of multiple single cells. Several approaches exist to generate these 3D spheroids including hanging droplet plates, spinner flasks, and microfluidic devices including microwells and droplet generators. These different methods to generate spheroids take advantage of two approaches: (1) prevention of cellular settling by coating the surface to facilitate the self-aggregation of cells into a spheroid and (2) utilizing polymer hydrogels to act a physical scaffold to allow for 3D cellular proliferation. While the former approach can generate 3D spheroids rapidly, they are highly heterogeneous and susceptible to disruption by fluid shear stress due to the lack of an ECM mimic to provide structure and stability. Conversely, biological and synthetic hydrogels can recapitulate the native ECM and encompass biophysical properties and biological functions found under in vivo conditions.

Hydrogels are widely used in biomedical research due to their biocompatibility, high water content, and high permeability for different growth factors and metabolites. Biological hydrogels such as collagen, Matrigel, and fibrin have specific biophysical and cell adhesive properties to mimic the ECM; however, they suffer from batch-to-batch variability and uncontrolled degradation which can affect reproducibility. Synthetic hydrogels like polyethylene glycol (PEG) and alginate offer excellent control and reproducibility but require external initiation to fully crosslink the materials to produce the resulting hydrogel. In fact, PEG is currently one of the most widely used monomers to synthesize hydrogels that is also FDA-approved.

Synthetic hydrogels are commonly synthesized using two approaches. The first method involves the chemical crosslinking of the polymer using photopolymerization, click reactions, enzyme catalysis or Michael-type reactions. The second approach uses physically crosslinked hydrogels that form due to hydrophilic-hydrophobic or dipole-dipole interactions. While each of these approaches has found success for 3D cell culture applications, they are not without limitations. Physically-crosslinked hydrogels are usually mechanically weaker and less stable than chemically-crosslinked hydrogels. Photopolymerized hydrogels can result in exogenous reactive radicals, reactive macromers, or initiators in the hydrogel which can adversely affect cell viability. In addition, rapid photopolymerization processes can increase the local temperature within the hydrogel, which also decreases cell viability.

Despite advances in 3D cell culture research, there is still a scarcity of hydrogel systems that are biocompatible and biodegradable, are non-cytotoxic, and have tunable properties such as stiffness, gelation time, swelling ratio, and diffusion coefficient of small molecules. These needs and other needs are satisfied by the present disclosure.

SUMMARY

In accordance with the purpose(s) of the present disclosure, as embodied and broadly described herein, the disclosure relates to thiol-acrylate hydrogels, methods of making the same, three-dimensional cell culture scaffolds comprising the same, systems for cell culture using the same, and methods of culturing cells, including cancer cells, using the same.

An aspect of the present disclosure includes a tunable cell culture material including a hydrogel, wherein the hydrogel is a product of a reaction between a thiol and an acrylate. The thiol can include ethoxylated trimethylolpropane tri (3-mercapto-propionate) (ETTMP), and the acrylate can include poly(ethylene glycol) diacrylate (PEGDA).

An aspect of the present disclosure includes a method for culturing cells. The method can include providing a tunable cell culture material as above and seeding the cells in the hydrogel to form a seeded hydrogel. The hydrogel can be contacted with a culture medium, then the cells can be allowed to grow for a period of from about 4 days to about 17 days.

Another aspect of the present disclosure includes a system for 3D cell culture that includes a microfluidic droplet-generating device and a thiol-acrylate hydrogel.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A shows a synthesis scheme of thiol-acrylate hydrogels generated by a base-catalyzed Michael addition at room temperature in accordance with embodiments of the present disclosure and FIG. 1B shows a schematic representation of ETTMP (three arm thiol) and PEGDA cross-linking (two arm acrylate) resulting in bonding of the thiol to the acrylate when the reaction is stoichiometrically balanced (i) and when there is excess thiol (ii).

FIG. 2A shows FTIR characterization of PEGDA, ETTMP and thiol-acrylate hydrogel in accordance with embodiments of the present disclosure. FIG. 2B shows a swelling profile of thiol-acrylate hydrogel in cell culture media at 37° C. in accordance with embodiments of the present disclosure. Hydrogel swelling ratio was monitored as a function of weight percentage of polymer (8.5, 9.0, and 9.5%) and molar ratio of thiol-to-acrylate groups (1.0 and 1.05) for 24 h.

(FIG. 11A) Three formulations (F1, F3, and F5) with a molar ratio of 1.0. (FIG. 11B) Three formulations (F2, F4, and F6) with a molar ratio of 1.05. Black lines and data points are for G' and red lines and data points are for G".

FIG. 15 shows a two-layer PDMS microfluidic droplet generator in accordance with embodiments of the present disclosure. The bottom layer contains a trapping array, a microfluidic channel, and the top layer is a flat PDMS layer containing holes for inlets and an outlet.

FIGS. 16A-16D show generation of spheroid using a droplet generator system (also referred to as a system for 3D cell culture) in accordance with embodiments of the present disclosure. FIG. 16A is a top view of the droplet trapping array showing two inlets for carrier oil (1), cells in the aqueous hydrogel (2), a flow-focusing junction (3), the droplet trapping array (4), and the single outlet (5). FIG. 16B is a side view of the two-layer Polydimethylsiloxane (PDMS) device. FIG. 16C is a Brightfield image of MCF-7 cells trapped inside the hydrogel droplet in day 0 and FIG. 16D shows spheroids on day 5. The scale bar is 150 µm.

Figure 3:
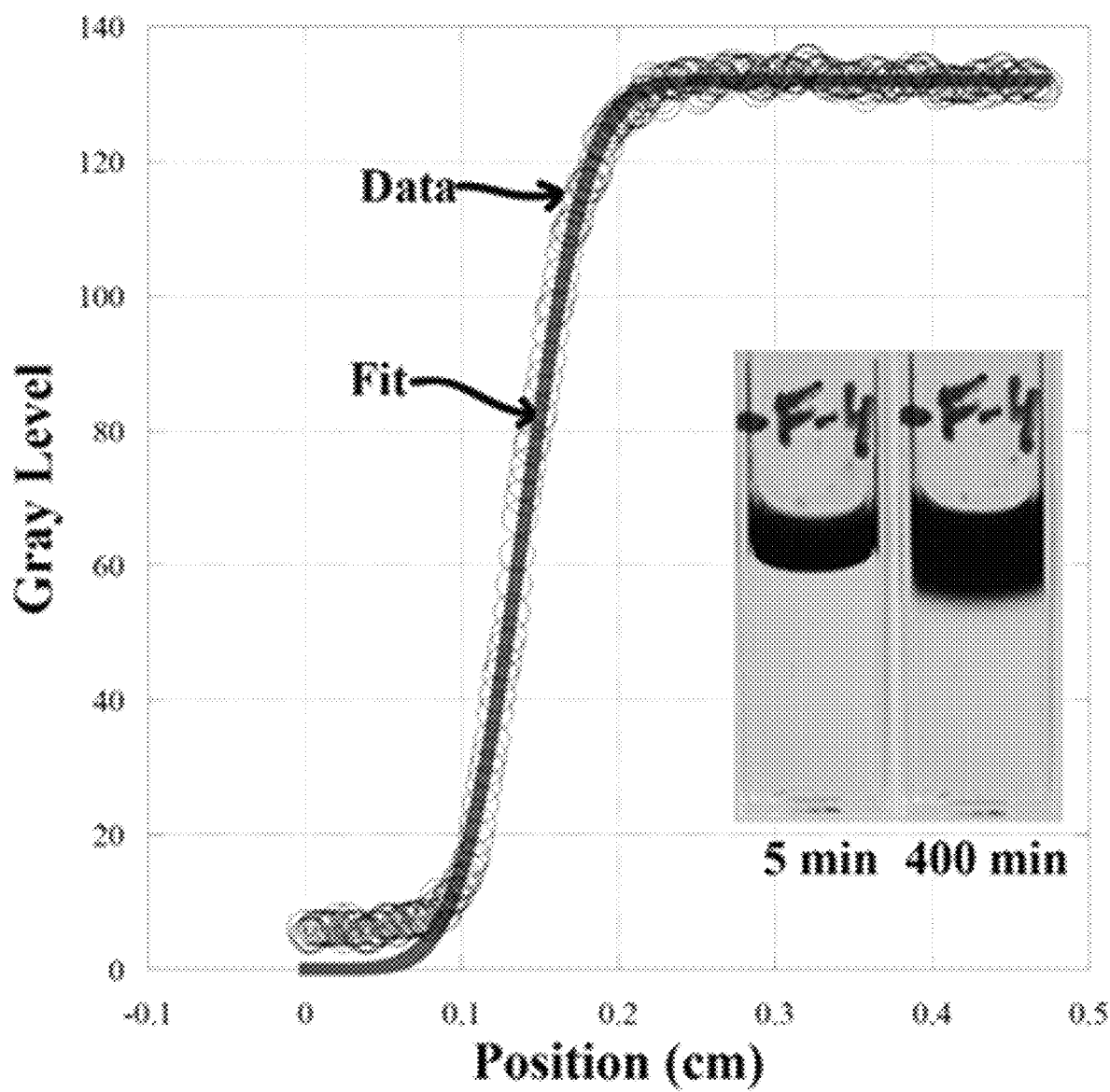
FIG. 3 shows diffusion of bromothymol blue into the thiol-acrylate hydrogel according to the present disclosure. The mass transfer of the dye is modeled by an error function which was numerically fit to the data using KaleidaGraph to calculate the diffusion coefficient (D). Data is for F2 at the 30 min time point which is representative of the mass transfer within all six hydrogels. (Inset) Images of the migrating front of the bromothymol blue dye in F4 at 5 and 400 min.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a buffer," "a thiol," or "an acrylate," includes, but is not limited to, combinations of two or more such buffers, thiols, or acrylates, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a thiol refers to an amount that is sufficient to achieve the desired improvement in the property modulated by the formulation component, e.g. achieving the desired level of cell viability in the resulting hydrogel. The specific level in terms of wt % in a composition required as an effective amount will depend upon a variety of factors including the amount and type of thiol, amount and type of acrylate, amount and pH of buffer, and end use of the hydrogel made using the composition.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

As used herein, a "thiol" is an organic compound containing an —SH group. In one aspect, thiols are useful for synthesizing the hydrogels disclosed herein. In another aspect, a molecule useful herein can have two or more thiol groups. In one aspect, the thiol used herein is ethoxylated trimethylolpropane tri (3-mercapto-propionate) (ETTMP):

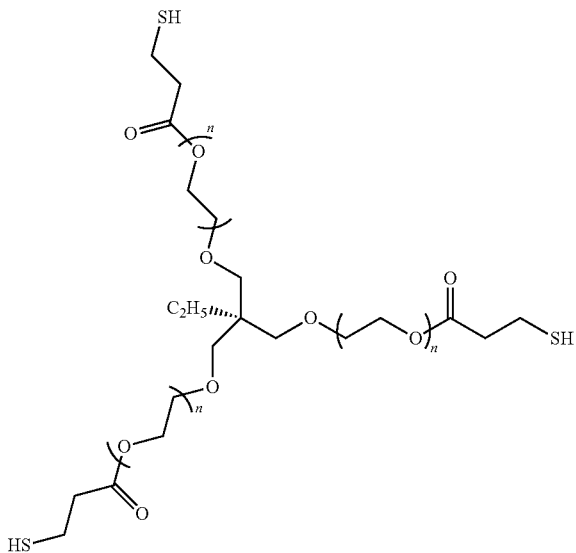

As used herein, an "acrylate" is a salt, ester, or conjugate base of acrylic acid and its derivatives. In another aspect, acrylates are useful for synthesizing the hydrogels disclosed herein. In still another aspect, a molecule useful herein can have two or more acrylate groups. In one aspect, the acrylate used herein is poly(ethylene glycol) diacrylate (PEGDA):

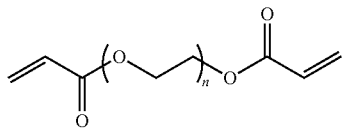

The "Michael reaction" or "Michael addition" is nucleophilic addition to an $\alpha,\beta$-unsaturated carbonyl compound. In one aspect, disclosed herein are hydrogels formed by the Michael addition between a thiol and an acrylate. In another aspect, disclosed herein are hydrogels formed by the Michael addition between ETTMP and PEGDA. In one aspect, the Michael addition disclosed herein requires a basic solution to proceed. In a further aspect, the reaction product between one thiol group and one acrylate group has the structure shown below:

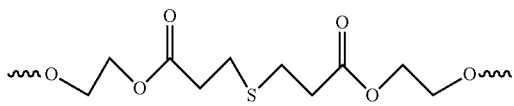

As used herein, a "hydrogel" is a network of hydrophilic polymer chains. When the polymer chains are held together by crosslinks, a three dimensional solid can form. In one aspect, the hydrogel has structural integrity because of the presence of the crosslinks. In another aspect, a hydrogel is highly absorbent but does not dissolve in water. In one aspect, disclosed herein are hydrogels formed from the Michael addition of thiols and acrylates.

As used herein, "crosslinking" refers to a process by which polymeric chains are extended in a multidimensional manner. In one aspect, crosslinking results in a network or 3D structure. Crosslinking can be covalent or ionic, and restricts the ability of a polymer network to move. In one aspect, crosslinking of a polymer that typically dissolves or exists in a liquid state can form a solid or gel out of the polymer. In one aspect, disclosed herein are covalently crosslinked hydrogels formed by the Michael addition of thiols and acrylates such as, for example, ETTMP and PEGDA.

"Initiation" as used herein is the first step of the polymerization process. In some aspects, a radical polymerization process initiates when an activating agent or external energy source (i.e., heat, UV irradiation) is used. In one aspect, the polymerization disclosed herein does not require a radical initiator or any source of external energy. In another aspect, initiation in the reactions disclosed herein occurs when an aqueous basic solution is added to the reaction mixtures disclosed herein.

"Photopolymerization" as used herein requires light (typically ultraviolet but visible light can also be used in some instances) to initiate and/or propagate a polymerization reaction. In some aspects, when living cells are incorporated into a hydrogel, the light used for photopolymerization can damage, mutate, or kill the cells. In one aspect, the polymerization process disclosed herein is not a photopolymerization process and/or does not require an external light source.

As used herein, "gelation" is the formation of a gel from a polymeric system. In a further aspect, branched or crosslinked polymers form a single macromolecule; the point at which this occurs is the system's gel point. At the gel point, or when gelation has occurred, at least some fluidity is lost while viscosity increases. Meanwhile, "gelation time" as referred to herein is the time period required for a hydrogel to form. In one aspect, gelation time can be measured by inverting a container containing a composition as disclosed herein; when a bubble will no longer traverse the contents of the container, gelation can be said to have occurred. In a further aspect, gelation time can be tuned by varying the ratio of thiol to acrylate in the compositions disclosed herein.

"Rigidity" or "stiffness" as used herein is a property of a hydrogel. In one aspect, when a hydrogel contains, serves as a scaffold for, or otherwise contacts cells, stiffness of the hydrogel can affect cell motility and/or differentiation, as well as cell viability. In some aspects, G' as discussed above is a measure of stiffness (or, conversely, elasticity) of the hydrogels disclosed herein. In some aspects, stiffness does not affect two-dimensional cell culture but a high degree of stiffness may be undesirable for three-dimensional cell culture on the hydrogels disclosed herein.

"Diffusion coefficient" is a measure of the amount of a substance that passes through each unit of cross section of a bulk material per unit of time. Diffusion coefficient for a given substance will be different depending on the properties such as, for example, stiffness, of the bulk material into which it is diffusing. In one aspect, diffusion coefficient can be used as an approximation of mass transfer of biomolecules in the hydrogel formulations disclosed herein. In another aspect, mass transfer of biomolecules through the hydrogels disclosed herein is important to cell reproduction and viability, when the hydrogels are used for two-dimensional or three-dimensional cell culture.

"Swell ratio" or "swelling ratio" as used herein is inversely related to the crosslinking density of a hydrogel. In some aspects, swell ratio is related to stiffness and diffusion rate of biomolecules into a hydrogel. In one aspect, swelling ratio can be calculated by dividing swollen gel rate at a specified time by dried gel weight.

"Shear storage modulus" (represented as G') as used herein refers to the elastic (in phase) stress to strain ratio of a material in response to an oscillatory stress. Storage modulus relates to a material's ability to store energy elastically and provides information about the amount of structure a material possesses and/or its resistance to deformation.

"Shear loss modulus" (represented as G") as used herein refers to the viscous (out of phase) component of oscillatory stress. Loss modulus relates to a material's ability to dissipate stress through heat and provides information about the amount of energy dissipated in a material. When G'>G", a material is primarily elastic. When G">G', externally applied forces cause a material to flow.

"Complex shear modulus" (represented as G*) relates to gel stiffness under dynamic conditions of deformation, regardless of whether the deformation is elastic or viscous. In one aspect, G*=G'+iG" where i is the imaginary unit. In one aspect, G* is a material property that relates complex shear stress and complex shear strain.

"Delta (δ)" is the phase angle difference between applied stress and deformation (strain). In one aspect, tan δ=G"/G'. In one aspect, tan δ serves as an indication of the degree of energy dissipation or damping of a material. A higher value (i.e., >1) for tan δ indicates that a material has more liquid-like properties, while a lower value (i.e., <1) for tan δ indicates that a material has more solid-like properties.

As used herein, "spheroid" refers to a three-dimensional, well-rounded aggregation consisting of multiple single cells. In one aspect, a spheroid can be used for three-dimensional culture for cancer cells. Numerous methods exist for generating spheroids including hanging droplet plates, spinner flasks, and microfluidic devices. In one aspect, prevention of cellular settling can facilitate self-aggregation of cells into a spheroid. In an alternative aspect, a polymer hydrogel can be used as a physical scaffold to allow for three-dimensional cellular proliferation. In a further aspect, use of a polymer hydrogel scaffold as in the techniques disclosed herein can mimic extracellular matrix and more closely resembles conditions found in vivo.

"Extracellular matrix" is a three-dimensional network of macromolecules, typically proteins or glycoproteins (e.g., collagen, enzymes, fibrous proteins) and polysaccharides. Extracellular matrix (or ECM) is implicated in cell communication, cell differentiation, and cell adhesion. In one aspect, the hydrogel formulations disclosed herein can mimic the extracellular matrix.

"Biocompatible" materials, as used herein, are materials that are not harmful to living tissues and/or cells. In one aspect, biocompatible materials do not elicit an immune response. As used herein, "cytotoxicity" is a property of a compound wherein the compound will ultimately cause cell death through any number of means including, but not limited to, necrosis, lysis, apoptosis, or a cessation of growth and division. Cytotoxicity is dependent upon cell type; what is cytotoxic to one cell may not be to another. In one aspect, materials that are biocompatible are not cytotoxic. In another aspect, the hydrogels disclosed herein are biocompatible and are not cytotoxic.

"Cell viability" refers to the quantification of the number of living cells (still carrying out normal metabolic activities) in a cell culture. In one aspect, cell viability can be expressed as a percentage of the total number of cells in a sample, where some cells may be dead. In one aspect, cytotoxicity of a substance can be assessed by performing a cell viability assay.

Methods of Making Thiol-Acrylate Hydrogels

In one aspect, disclosed herein are hydrogels formed via a Michael addition of a thiol with an acrylate. In some aspects, starting materials can have multiple thiol and/or multiple acrylate functional groups in order to facilitate crosslinking and formation of three-dimensional structures. In one aspect, the thiol-bearing molecule can have at least three thiol groups. In another aspect, the acrylate-bearing molecule can have at least two acrylate groups. In one aspect, the thiol is ethoxylated trimethylolpropane tri (3-mercapto-propionate) (ETTMP) and the acrylate is poly (ethylene glycol) diacrylate (PEGDA).

In one aspect, the PEDGA can have a number average molecular weight ($M_n$) of from about 400 to about 4000 Da, or of about 400, 500, 600, 700, 800, 900, 1000, 1250, 1500, 1750, 2000, 2250, 2500, 2750, 3000, 3250, 3500, 3750, or about 4000 Da, or a combination of any of the foregoing values, or a range encompassing any of the foregoing values. In one aspect, the PEGDA has an $M_n$ of about 700 Da.

In one aspect, different weight percentages of starting monomers can be used in order to fine-tune the properties (i.e., viscosity, swelling ratio, gelation time, and the like) of the hydrogels disclosed herein. In one aspect, the weight percentage of monomers can be from about 7 to about 11, or can be from about 8.5 to about 9.5, or can be about 7. 7.25, 7.5, 7.75, 8, 8.25, 8.5, 8.75, 9, 9.25, 9.5, 9.75, 10, 10.25, 10.5, 10.75, or about 11, or a combination of any of the foregoing values, or a range encompassing the foregoing values. In one aspect, the weight percentage of monomers is 8.5, 9, or 9.5.

In another aspect, different ratios of thiol to acrylate can be used in order to fine-tune the properties of the hydrogels disclosed herein. In another aspect, the ratio of thiol groups to acrylate groups can be from about 0.95 to about 1.10, or can be from about 1 to about 1.05, or can be about 0.95, 1.0, 1.05, or about 1.10, or a combination of any of the foregoing values, or a range encompassing the foregoing values. In one aspect, the ratio of thiol groups to acrylate groups is 1.0 or is 1.05.

In still another aspect, disclosed herein is a process for preparing thiol-acrylate hydrogels. In a further aspect, the Michael addition reaction can proceed in any suitable buffer. In one aspect, the buffer can be an extracellular buffer or ECB. In a still further aspect, the ECB is an aqueous solution of 5.036 mM HEPES, 136.89 mM NaCl, 2.68 mM KCl, 2.066 mM $MgCl_2.6H_2O$, 1.8 mM $CaCl_2.2H_2O$, and 5.55 mM glucose.

In one aspect, the pH of the buffer used can be adjusted to a higher or lower value using an appropriate base or acid as needed. In one aspect, the buffer pH is adjusted to from about 7.5 to about 8.2, or to about 7.5, 7.55, 7.6, 7.65, 7.7, 7.75, or about 7.8, or a combination of any of the foregoing values, or a range encompassing the foregoing values. In one aspect, the buffer pH is adjusted to 7.66. In any of these aspects, a slightly basic pH for the buffer may be required for initiation of the Michael reaction. In a further aspect, the buffer pH is adjusted with NaOH, KOH, or another commonly-used base. In one aspect, the buffer pH is adjusted with 5 mM NaOH. Advantageously, because the hydrogels described herein are crosslinked by a base-catalyzed Michael addition, the hydrogel does not require any external initiation.

In one aspect, following preparation and pH adjustment of the buffer, PEGDA can be added to the buffer and mixed by any suitable means. In one aspect, the PEGDA solution in buffer is vortexed for from about 10 seconds to about 30 seconds, or for about 10, 15, 20, 25, or about 30 seconds, or a combination of any of the foregoing values, or a range encompassing any of the foregoing values. In one aspect, the PEGDA solution in buffer is vortexed for about 15 seconds.

In another aspect, following complete dissolution of PEGDA in the buffer, ETTMP is added to the PEGDA-buffer mixture. In another aspect, the solution of PEGDA, buffer, and ETTMP can be mixed by any suitable means. In one aspect, the solution of PEGDA and ETTMP in buffer can be vortexed for from about 15 seconds to about 90 seconds, or can be vortexed for about 15, 30, 45, 60, 75, or about 90 seconds, or a combination of any of the foregoing values, or a range encompassing any of the foregoing values. In one aspect, the solution of PEGDA and ETTMP in buffer is vortexed for about 1 minute.

In any of the above aspects, following mixing of the PEGDA and ETTMP in buffer, the solution can be left undisturbed for a sufficient period to achieve gelation.

Properties of the Thiol-Acrylate Hydrogels

Gelation Time

In one aspect, gelation time for the hydrogels disclosed herein can be from about 10 to about 300 minutes, or from about 25 to about 180 minutes, or can be about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or about 300 min, or a combination of any of the foregoing values, or a range encompassing any of the foregoing values. In one aspect, the gelation time is 10 minutes, 25 minutes, 40 minutes, 180 minutes, or 300 minutes. In another aspect, gelation time correlates with monomer percentage and ratio of thiol to acrylate. In one aspect, a faster gelation time may result in the formation of a stiffer hydrogel. Thus, in one aspect, a somewhat slower gelation time, resulting in a hydrogel with less stiffness, is preferred for three-dimensional cell culture applications. In some aspects, a molar ratio of components of 1.05 (i.e., ratio of thiol groups to acrylate groups) as disclosed herein can lead to a gelation time of from about 25 to about 40 minutes, or in some cases from about 25 to about 60 minutes. In other aspects, a molar ratio of components of 1.0 can lead to a gelation time of from about 30 to about 150 minutes, or from about 25 to about 180 minutes in some cases.

Swell Ratio

In another aspect, swelling ratio for the hydrogels disclosed herein can be determined by weighing the hydrogel when dried, incubating the hydrogel in culture medium (such as, for example, ECB), and weighing the rehydrated hydrogel, then taking the ratio of rehydrated hydrogel to dried hydrogel. In one aspect, the hydrogels disclosed herein can be dried by leaving them out overnight at room temperature. In another aspect, incubation in culture medium typically takes place at about 37° C. In one aspect, swell ratio after 4 hours of rehydration can be from about 2 to about 5, or can be from about 2.5 to about 4.5, or can be about 2, 2.5, 3, 3.5, 4, 4.5, or about 5, or a combination of any of the foregoing values, or a range encompassing any of the foregoing values. In another aspect, swell ratio after 24 hours of rehydration can be from about 0.5 to about 8, or can be from about 1 to about 7, or can be about 0.5, 1, 1.5, 2, 2.5, 3, 3.5, 4, 4.5, 5, 5.5, 6, 6.5, 7, 7.5, or about 8, or a combination of any of the foregoing values, or a range encompassing any of the foregoing values.

Diffusion Coefficient

In another aspect, diffusion coefficient for biomolecules can be calculated for the hydrogels disclosed herein. In a further aspect, diffusion coefficient for a model system can be used to approximate diffusion and/or mass transfer behavior for other molecules important for applications such as, for example, cell culture.

In one aspect, an example molecule can be dissolved in water or in ECB or another suitable buffer. In one aspect, the molecule has a color in solution that can be observed by eye and/or photographed with a camera. In a further aspect, the molecule can be at a concentration of about 1% (w/w) in the water. In a still further aspect, the solution of molecule in water can be dropped on a hydrogel formed in a plastic cuvette. In some aspects, diffusion of the molecule can be photographed at any desired interval. Photographic data can be quantified such that it is assumed gray level intensity is proportional to model molecule concentration; in one aspect, gray level intensity versus vertical position can be modeled to determine diffusion coefficient. Exemplary procedures for calculating diffusion coefficient can also be found in the Examples.

In one aspect, diffusion coefficient can be from about 5 to about $10 \times 10^{-8}$ $cm^2/s$, or can be about 5, 5.5, 6, 6.5, 7, 7.5, 8, 8.5, 9, 9.5, or about $10 \times 10^{-8}$ $cm^2/s$, or a combination of any of the foregoing values, or a range encompassing any of the foregoing values. In another aspect, diffusion coefficient can be about 6.3, 6.5, 6.7, 7.2, 9.4, or $9.5 \times 10^{-8}$ $cm^2/s$.

Degradation of Hydrogels

In some aspects, it may be valuable to know the conditions under which the hydrogels disclosed herein degrade, and the extent to which they degrade, as well as over what time period this degradation can happen. In one aspect, hydrogels can be weighed prior to degradation experiments to establish an initial weight. The hydrogels can then be incubated at 37° C. in 5% $CO_2$ in a suitable buffer in a humidified incubator for a desired period of time, the surrounding solution removed, and the hydrogels weighed again to obtain a degraded weight. If additional degradation studies are desired, in one aspect, the solution can be added back to the weighed samples and they can be placed in the incubator for an additional time period.

In any of the above aspects, a high pH buffer or medium can be used for degradation studies. In one aspect, ester hydrolysis rates increase at higher pH levels. In one aspect, the buffer or medium can be Dulbecco's Modified Eagle Media (DMEM) with a pH of 8.05. In an alternative aspect, the buffer or medium can be phosphate-buffered saline (PBS) with a pH of 7.9. In some aspects, the buffer or medium can contain an antibiotic such as, for example, penicillin or streptomycin to prevent bacterial contamination during the degradation study. In one aspect, an amount of DMEM or PBS as described above can be placed on the hydrogel and the hydrogel can then be placed in the incubator under the conditions previously described.

In one aspect, when the buffer or medium is DMEM, complete degradation of the hydrogels takes from about 40 to about 200 hours, or from about 60 to about 150 hours, or about 40, 50, 60, 70, 80, 90, 100, 110, 120, 130, 140, 150, 160, 170, 180, 190, or about 200 hours, or a combination of any of the foregoing values, or a range encompassing any of the foregoing values. In another aspect, when the buffer or medium is PBS, complete degradation of the hydrogels takes from about 50 to about 500 hours, or from about 100 to about 425 hours, or about 50, 75, 100, 125, 150, 175, 200, 225, 250, 275, 300, 325, 350, 375, 400, 425, 450, 475, or about 500 hours, or a combination of any of the foregoing values, or a range encompassing any of the foregoing values. As used herein, complete degradation means that the relative weight of the material decreases to no greater than one millionth of an original weight of the material or about zero. Additional exemplary procedures for assessing hydrogel degradation rates can be found in the Examples.

Rheology

In one aspect, the rheological properties of the hydrogels disclosed herein can be measured from bulk sample deformation using a rheometer. In a further aspect, rheological properties can be determined by any suitable method able to subject the hydrogels to oscillatory stress and determine their response. In one aspect, small amplitude oscillatory shear can be implemented. In a further aspect, a parallel disc rheometer can be used. In a further aspect, the parallel discs can be 8 mm in diameter. In any of these aspects, the rheological properties can be determined at any desired temperature. In one aspect, since it is desired to use the hydrogels as cell culture media for human cancer cells, rheological properties can be determined at 37° C. so as to more accurately reflect conditions in the human body. In a further aspect, a frequency range of from about 0.65 to about 65 rad/s can be used, or from about 0.682 to about 62.8 rad/s can be used, or about 0.65, 0.75, 0.85, 0.95, 1, 2, 3, 4, 5, 10, 15, 20, 25, 30, 35, 40, 45, 50, 55, 60, or about 65 rad/s can be used, or a combination of any of the foregoing values, or a range encompassing any of the foregoing values. In another aspect, a constant shear strain amplitude of from about 7% to about 13%, or of about 7, 8, 9, 10, 11, 12, or about 13% can be used, or a combination of any of the foregoing values, or a range encompassing any of the foregoing values. In one aspect, rheological properties can be measured under a constant shear strain amplitude of about 10%.

In a further aspect, $G^*$ and $\tan \delta$ as described previously can be measured as proxies for material stiffness. In some aspects, when $0 \leq \tan \delta \leq 1$, a material is purely elastic. In other aspects, when $\tan \delta > 1$, a material acts as a viscous liquid. In any of these aspects, when angular frequency is between about 1 and 100 rad/s, $\tan \delta$ is from about 0.01 to about 10, or is about 0.01, 0.025, 0.05, 0.075, 0.1, 0.25, 0.5, 0.75, 1, 2, 3, 4, 5, 6, 7, 8, 9, or about 10, or a combination of any of the foregoing values, or a range encompassing any of the foregoing values. In another aspect, when angular frequency is between about 1 and 100 rad/s, $G^*$ is from about 10 to about 1000 Pa, or is about 10, 25, 50, 100, 150, 200, 250, 300, 350, 400, 450, 500, 550, 600, 650, 700, 750, 800, 850, 900, 950, or about 1000 Pa, or a combination of any of the foregoing values, or a range encompassing any of the foregoing values. Additional exemplary procedures for measuring and/or calculating rheological properties can be found in the Examples.

Cell Culture Using the Thiol-Acrylate Hydrogels

Cell Viability Assays

In one aspect, in either two-dimensional or three-dimensional cell culture methods using the hydrogels disclosed herein, cell viability can be assessed using any method known in the art. In one aspect, a cell viability assay includes using Calcein AM to identify living cells. In a further aspect, Calcein AM is a non-fluorescent, hydrophobic compound that permeates intact, living cells. Further in this aspect, intracellular esterases produce calcein, a hydrophilic fluorescent compound that is retained in the cytoplasm. In another aspect, ethidium homodimer-1 can be used to identify dead cells. In one aspect, a 3.5 µM solution of Calcein AM in ECB is used to assess cell viability. Ethidium homodimer-1 (EthD-1) is a stain with a high affinity for nucleic acids that emits red fluorescence once bound to a nucleic acid. In one aspect, EthD-1 cannot enter a living cell because the living cell does not have a compromised membrane. In another aspect, dead cells have disrupted membranes, thus giving EthD-1 the ability to enter and bind to DNA. In one aspect, EthD-1 can stain dead cells regardless of the method of cell death (e.g., lysis, apoptosis, etc.). In one aspect, a 3.85 µM solution of EthD-1 in ECB is used to assess the number of dead cells present in a sample.

In another aspect, cells can be cultured for any length of time desired prior to assessing cell viability. In one aspect, cells are cultured at 37° C. with 5% $CO_2$ in a humidified incubator for up to 9 days. Further in this aspect, complete media can be replenished at intervals to ensure sufficient nutrients were present for the cells. In any of the above aspects, to assess viability, staining solution can be added to the samples where the assessment is desired, the mixture of sample and staining solution can be incubated for up to 70 minutes in the dark, and visualization can be accomplished using fluorescence microscopy. In some aspects, a microscope camera can be used with a FITC filter (green, for live cells) or a rhodamine filter (red, for dead cells).

In any of the above aspects, all vortexing of hydrogel preparations is conducted prior to the addition of cells to avoid problems with cellular shearing. If desired, in one aspect, a cell/hydrogel suspension can be gently mixed using a micropipette to ensure a homogeneous distribution of cells.

Two-Dimensional Cell Culture

In one aspect, two-dimensional cell culture can be used as an initial measure of hydrogel biocompatibility and/or cytotoxicity to avoid issues regarding mass transfer of nutrients. In one aspect, in two-dimensional cell culture situations, a 1.05 molar ratio of thiol groups to acrylate groups results in a sample wherein from about 90 to about 100% of cells remain viable after 4, 7, 11, 17, or 24 days. In another aspect, from about 95 to about 97% of cells remain viable, or about 90, 91, 92, 93, 94, 95, 96, 97, 98, 99, or about 100% of cells remain viable, or a combination of any of the foregoing values, or a range encompassing any of the foregoing values. In another aspect, after about 36-48 hours, triple negative breast cancer cells (MDA-MB-231) plated on a 1.05 molar ratio hydrogel migrated away from the seeding site and adopted the morphology typically seen with this cell type in other culture scenarios.

In another aspect, in two-dimensional cell culture situations, a 1.0 molar ratio of thiol groups to acrylate groups results in a sample where only from about 1 to about 10% of cells remain viable after 4, 7, 11, or 17 days. In another aspect, about 1 to about 5% of cells remain viable, or about 1, 2, 3, 4, 5, 6, 7, 8, 9, or about 10% of cells remain viable, or a combination of any of the foregoing values, or a range encompassing any of the foregoing values. In one aspect, a 1.0 molar ratio of thiol to acrylate groups can prevent cell attachment to the hydrogel. In another aspect, a 1.0 molar ratio of thiol to acrylate groups may be considered cytotoxic. In another aspect, triple negative breast cancer cells (MDA-MB-231) plated on a 1.0 molar ratio hydrogel remained at the site of deposition and never adopted the morphology associated with this cell type.

In one aspect, weight percentage of hydrogel monomers does not impact cell viability, morphology, or spreading in two-dimensional culture.

Three-Dimensional Cell Culture

In one aspect, similarly to the two-dimensional results, none of the hydrogels with a 1.0 molar ratio of thiol to acrylate is able to sustain cell viability for 17 days in three-dimensional cell culture conditions. Without wishing to be bound by theory, this may be due to faster degradation times of these hydrogel formulations; rapid degradation may be incompatible with cell spreading on hydrogels. In a further aspect, unlike with the two-dimensional results, weight percentage of hydrogel monomers can have an impact on cell viability in three-dimensional cell culture conditions. In one aspect, cells seeded within formulations having lower weight percentages (e.g., 8.5% and 9%) grew and remained viable after 17 days of culture. In some aspects, in these formulations cells formed aggregates with a mixture of living and dead cells. In one aspect, about 60% of cells are viable after 17 days.

In another aspect, cells plated on hydrogels with higher weight percentages (e.g., 9.5%) may exhibit lower viability than cells plated on lower weight percentage hydrogels. In one aspect, the 9.5% hydrogels are stiffer than those with lower weight percentages. Further in this aspect, stiffer hydrogels may not facilitate growth conditions necessary for cell viability.

In any of the above aspects, isolated cancer cells were less likely to be proliferative and more likely to be dead by the end of the culture period. In another aspect, cells seeded near to one another in groups were more likely to survive under any of the experimental conditions described herein. In one aspect, cells can be seeded on top of the hydrogels. In an alternative aspect, cells can be seeded inside the hydrogels. Further in this aspect, when cells are seeded inside the hydrogels, the cells can survive for from at least 4 to at least 12 days, or for 4, 5, 6, 7, 8, 9, 10, 11, or 12 days, or a combination of any of the foregoing values, or a range encompassing any of the foregoing values.

In one aspect, three-dimensional cell culture as disclosed herein can occupy any standard well plate or culture dish intended for cell culture. In one aspect, a 6-well, 12-well, 24-well, or 48-well plate can be used, or a culture dish of any diameter including 35 mm, 60 mm, or 100 mm. Further in this aspect, gel volume can be from about 100 μL to about 10 mL, or can be about 100, 200, 300, 400, 500, 600, 700, 800, or 900 μL, or about 1, 2, 3, 4, 5, 6, 7, 8, 9, or about 10 mL, or a combination of any of the foregoing values, or a range encompassing any of the foregoing values. In one aspect, gel volume can be about 100 μL, about 200 μL, about 3 mL, or about 6.5 mL.

Microfluidic Device for Cell Culture

In some aspects, the microfluidic device includes a microfluidic droplet trapping array. In one aspect, the microfluidic droplet trapping array can generate 100-300 μm aqueous droplets containing single cells encapsulated by the thiol-acrylate hydrogels disclosed herein. Advantageously, polymerization of the hydrogel takes place during droplet generation and trapping, resulting in a rapid encapsulation of the cells. In a further aspect, the droplets disclosed herein can be used for drug screening and/or basic research into processes occurring in diseases such as, for example, cancer and heart disease.

In some aspects, the microfluidic droplet-generating device can be used as system for 3D cell culture that includes a thiol-acrylate hydrogel for cell seeding.

In one aspect, the microfluidic droplet-generating device includes a droplet trapping array located below a flow channel. The trapping array can include a plurality of circular traps having a diameter of about 70 μm to about 300 μm. For example, the diameter of each circular trap can be about 70 μm, about 150 μm, or about 300 μm. In particular aspects, the trapping array can have about 785 traps having a diameter of 70 μm each, about 990 traps having a diameter of 150 μm each, or about 450 traps having a diameter of 300 μm each. Other sizes and quantities can be envisioned by one of ordinary skill in the art.

In some aspects, the microfluidic droplet-generating device includes a flat layer having two inlets and an outlet. The flat layer is above a bottom PDMS device layer that includes microfluidic flow channels and a trapping array, such the that the trapping array is provided below the flow channels.

In one aspect, the microfluidic device has two inlets, one for oil and another for unpolymerized hydrogel containing cells. Further in this aspect, flow from each inlet can be adjusted to select a droplet size. In a further aspect, following droplet generation, growth media can be used to flush oil out of the device and to transfer droplets to a trapping array where further experiments can be conducted while the droplets are maintained in place.

Cell Culture in a Microfluidic Device Using the Thiol-Acrylate Hydrogels

Although spheroids are useful for three-dimensional cell culture, they can still exhibit heterogeneity in terms of size and cellular distribution when generated from multiple cells. In one aspect, disclosed herein is a method for generating large numbers of three-dimensional spheroids from a single progenitor cell. In a further aspect, the method makes use of microfluidic devices to generate uniform spheroids. Advantageously, the spheroids generated by the methods described herein can exhibit greater homogeneity than spheroids generated by existing methods. In a still further aspect, a thiol-acrylate based hydrogel as described above in conjunction with a microfluidic device can serve as the basis for rapid, facile generation of three-dimensional spheroids.

In one aspect, cells can occupy from about 10% to about 20% of the hydrogel volume, or can be about 10, 11, 12, 13, 14, 15, 16, 17, 18, 19, or about 20% of the hydrogel volume, or a combination of any of the foregoing values, or a range encompassing any of the foregoing values.

In some aspects, the hydrogels used in microfluidic devices can incorporate biomolecules such as, for example, RGD peptide (i.e., arginylglycylaspartic acid), which is in some aspects responsible for cell adhesion to the extracellular matrix, or hyaluronic acid, which can modulate the flowability and/or viscosity of the extracellular matrix. In a further aspect, incorporation of these biomolecules better recreates the three-dimensional cellular environment for cell culture purposes.

In some aspects, a method for generating spheroids includes using the hydrogels and microfluidic droplet-generating devices described herein. Air can be removed from the device by injecting a non-flammable heat transfer fluid (referred to herein as an oil) into the inlet and flowing through the device. In some aspects, the oil can be Novec™ 7500 (3M™). A material including thiol acrylate hydrogel mixed with cells of interest is injected into an inlet of the device until the traps in the trapping array are filled. Excess material is flushed from the device by a second flowing of oil, and the material is allowed to polymerize. In some aspects, the thiol acrylate hydrogel is a 8.5 wt. % thiol acrylate hydrogel. A culture growth media is flowed into the device to flush remaining oil and to sustain cell growth and proliferation. The growth media can be flowed for about 24 to 48 hours. In some aspects, a gravity-flow setup can be used to allow growth media to continually flow over the trapped droplets (a.k.a. spheroids). In some aspects, the growth media can be paused for a period of about 24-48 hours, and then resumed at intervals for periodic feeding (e.g. in about 24-hour intervals).

The method is tunable based on the desired outcome. Larger spheroids (e.g. about 50-100 or more cells) can be generated faster using larger trapping arrays, but may be more heterogeneous due to the larger span of genotypes arising from a larger number of initial cells. Smaller spheroids (e.g. about 4 to about 10 cells in a 150 um droplet) that are more homogeneous can be generated, but the process takes more time for the smaller spheroid to grow into a larger spheroid. The generated spheroids can be used in an array of on-chip or other experiments.

Advantageously, the process for generating spheroids is rapid. Droplets in the aqueous phase can be achieved within 10 minutes from the mixture of the unpolymerized hydrogel and cells to droplet formation in the device. The completion of gelation (polymerization) of the aqueous thiol-acrylate reaction mixture occurs in the trapping array in about 35 minutes.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods Used in Examples

Chemicals

Polyethylene glycol diacrylate (PEGDA) ($M_n$ 700) was purchased from Sigma Aldrich. Ethoxylated trimethylolpropane tri(3-mercaptopropionate) 1300 (ETTMP 1300) was generously donated by Evans Chemetics LP. Extracellular buffer (ECB: 5.036 mM HEPES, 136.89 mM NaCl, 2.68 mM KCl, 2.066 mM $MgCl_2 \cdot 6H_2O$, 1.8 mM $CaCl_2 \cdot 2H_2O$, and 5.55 mM glucose) was used as the solvent for hydrogel synthesis. 5M NaOH was added to the buffer to bring it to a final pH of 7.66. Unless otherwise stated, all other reagents were obtained from Sigma Aldrich.

Cell Culture and Reagents

MDA-MB-231 is a triple-negative breast cancer cell line that has been shown to be very aggressive and drug resistant, whereas MCF7 is an ER-positive breast cancer cell line that is less aggressive and more susceptible to therapy. Both cell lines were maintained with Dulbecco's Modified Eagle Medium (DMEM) (Corning) supplemented with 10% v/v HyClone Cosmic Calf Serum (VWR Life Sciences Seradigm), 1% MEM Essential Amino Acids (Quality Biological Inc.), 1% MEM Non-Essential Amino Acids (Quality Biological Inc.), 1 mM sodium pyruvate (Thermo Fisher Scientific), and 6 μL insulin/500 mL media (Insulin, Human Recombinant dry powder, Sigma Aldrich). Cells were maintained in T-75 flasks in a humidified incubator at 37° C. and 5% v/v $CO_2$. Cells were subcultured when confluent by first washing the cells with 1× phosphate buffered saline (PBS: 137 mM NaCl, 10 mM $Na_2HPO_4$, 27 mM KCl, and 1.75 mM $KH_2PO_4$ at pH 7.4) and then detaching the cells with Trypsin-EDTA (Corning) and MCF-7 was with 1×PBS (137 mM NaCl, 10 mM $Na_2HPO_4$, 27 mM KCl, and 1.75 mM $KH_2PO_4$ at pH 7.4) prior to re-seeding into a new T-75 flask.

Example 2: Exemplary Hydrogel Synthesis

Three different weight percentages (8.5, 9, and 9.5%) of thiol-acrylate hydrogels, each with two different molar ratios of thiol groups to acrylate groups (1.0 and 1.05) were synthesized at room temperature (herein referred to as formulations 1-6, Table 1). To initiate the reaction, ~13-20 μL of 5M NaOH (depending upon the total volume of the hydrogel) was added to ECB which made the reaction basic enough for Michael addition (FIG. 1A); The PEGDA was then added to the ECB and vortexed for 15 seconds to disperse it in the buffer solution. Finally, the ETTMP was added and the complete reaction solution was vortexed vigorously for one minute and left undisturbed to complete the reaction. Gelation time was measured by regularly inverting the hydrogel in a tube. The gelation time was identified as the time at which a bubble would no longer rise in the hydrogel.

TABLE 1

Composition and Gelation Time of Different Thiol-Acrylate Hydroge Formulations

| Formulation | Weight % of Gel | Molar Ratio of Thiol to Acrylate Group | Gelation Time (min) |
| --- | --- | --- | --- |
| F1 | 8.5 | 1.0 | 150 |
| F2 | 8.5 | 1.05 | 40 |
| F3 | 9 | 1.0 | 80 |
| F4 | 9 | 1.05 | 30 |
| F5 | 9.5 | 1.0 | 30 |
| F6 | 9.5 | 1.05 | 25 |

NaOH was used to deprotonate a thiol group (—SH) into a thiolate (—S—), which then allows for the addition of an acrylate group. Increasing the amount of the thiol in the reaction mixture did maximize the reaction probability between thiol and acrylate. Additionally, adding excess thiol resulted in some uncrosslinked thiol groups (FIG. 1B, red arms shown in (ii), which may increase the hydrogel mesh size.

Figure 9A:
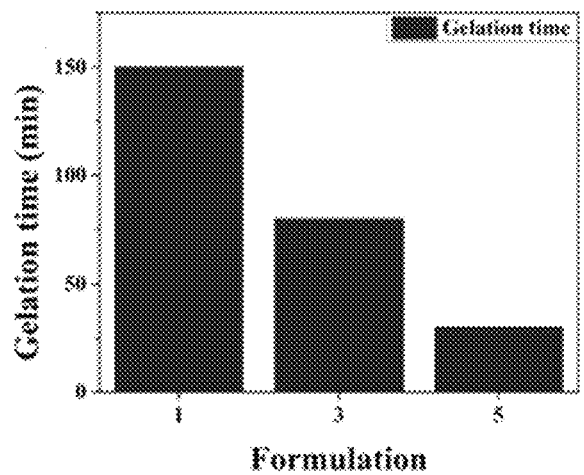
FIGS. 9A-9B show variation in gelation times for different formulations of thiol-acrylate hydrogels in accordance with embodiments of the present disclosure. Three different weight percentages were examined, 8.5% (F1/F2), 9.0% (F3/F4), and 9.5% (F5/F6), in addition to two different molar ratios of thiol-to-acrylate group is 1.0 (FIG. 9A) and 1.05 (FIG. 9B).
Figure 9B:
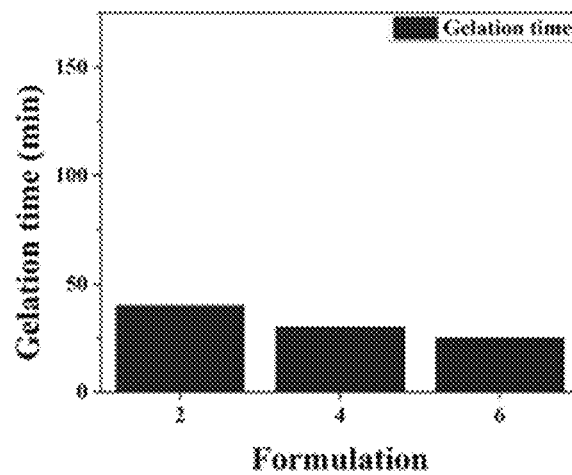

One requirement for an optimal hydrogel for 3D cell culture applications is the ability to quickly polymerize to allow for the addition of culture media to ensure no reduction in cellular viability. It was found that the gelation time of the thiol-acrylate hydrogels varied significantly by tuning the thiol-to-acrylate molar ratios and relative weight percentages of the two monomers (Table 1 and FIGS. 9A-9B). The gelation times were found to be inversely related to the weight percentages of the monomers present in the hydrogel. Increasing the weight percent from 8.5 to 9.5% resulted in a 5-fold decrease in gelation time from 150 min (F1) to 30 min (F5). This effect was not as prominent in the presence of excess thiol with only a 1.6-fold decrease in gelation time from 40 min (F2) to 25 min (F6).

The molar ratio of thiol-to-acrylate groups was found to be a factor in several aspects of the hydrogel. A large reduction in gelation time was observed by changing the ratio from 1.0 to 1.05; however, this effect was diminished with increasing monomer content. Additionally, altering the molar ratio from 1.0 to 1.05 resulted a higher degree of cellular viability and growth during 3D cell culture. Changing the molar ratio from 1.0 to 1.05 resulted in the two components actually reaching a stoichiometric ratio. The data presented here indicated that an inexpensive thiol (ETTMP) and acrylate (PEGDA) are able to generate stabile, noncytotoxic hydrogels without any need for purification of the chemicals.

Example 3: Characterization of Exemplary Hydrogels

FTIR Characterization

Thiol-acrylate hydrogel samples were dehydrated with acetone by placing a small amount of sample in a glass vial where it was serially soaked in 25, 50, 75, and 100% acetone for 30 min in each. Later, the samples were dried at room temperature overnight in negative 1 atm pressure. Finally, the FTIR spectra of monomers (PEGDA, ETTMP) and dried hydrogel were collected using a Bruker Tensor 27 FTIR spectrophotometer equipped with a Pike Miracle single bounce diamond attenuated total reflectance (ATR) cell. FTIR data confirmed that thiol-acrylate hydrogels were formed by reacting thiols with acrylate groups. However, in thiol-acrylate hydrogel spectra (FIG. 2A), some important IR bands are absent that were present in the spectra of monomers. Such bands are 2,560, 1,635, 1,408, 990, and 810 cm$^{-1}$, which are responsible for S—H stretching (thiol), C=C stretching (acrylate), =CH2 bending, =CH2 wagging, and =CH2 twisting, respectively, are absent in thiolacrylate hydrogel spectra.

Swell Ratio Determination

The swelling ratio is an important parameter of a hydrogel for biological applications as this ratio is inversely related to the crosslinking density of a hydrogel, which ultimately affects stiffness and diffusion rate of biomolecules into the hydrogel. Hydrogel weights were taken under three conditions: (i) immediately after the synthesis of the hydrogel, (ii) after the hydrogel was dried, and (iii) after the hydrogel was rehydrated with buffer to induced swelling. After complete gelation, the total weight of the hydrogel was obtained. Then the hydrogel was dried overnight at room temperature and weighed again ($W_d$). Then the hydrogel was rehydrated by immersing it in culture media followed by incubation at 37° C. for 24 hours. The sample weight of the rehydrated hydrogel was collected after 4 and 24 hours of incubation. The equilibrium weight swelling ratio (Q) was calculated using Eqn. 1:

$$Q = \frac{W_s}{W_d} \quad \text{Eqn. 1}$$

where $W_s$ is the swollen gel weight at a specified time interval and $W_d$ is the dried gel weight.

F1, F3, and F5 (1.0 molar ratio of thiol-to-acrylate) exhibited maximum swelling (equilibrium swelling) in culture media between 4 to 5 hours, whereas F2, F4, and F6 (1.05 molar ratio) reached their maximum swelling within in 24 hours (FIG. 2B). Among all six formulations, F2 exhibited the highest swelling ratio (close to 6).

Diffusion Coefficient Approximation

In addition to the transport of water into the hydrogel, the diffusive mass transfer of biomolecules is essential for proper cell proliferation and viability during 3D cell culture applications. To approximate the mass transfer of biomolecules into the thiol-acrylate hydrogels, the diffusion coefficient of bromothymol blue was measured (FIG. 3). A solution of 1 wt % bromothymol blue was made in deionized (DI) water. For this experiment, each hydrogel formulation was synthesized in a plastic cuvette (10×10×48 mm). Once the hydrogel solidified, 200 μL of 1% dye solution was carefully placed on top of the hydrogel. Images were collected every 60 min for 400 min using a Nikon D3200 (072 Dill TAMRON 18-270 mm). The grey level intensity versus vertical position in the cuvette was analyzed using ImageJ (NIH). The analysis assumed that the grey level intensity was proportional to dye concentration. The grey level profile along the vertical axis was fit to Eqn. 2, where y is position, t is time, and D is the diffusion coefficient:

$$C(y, t) = \frac{1}{2}\text{erf}\left(\frac{x}{2\sqrt{Dt}}\right) + \frac{1}{2} \quad \text{Eqn. 2}$$

At each time point, the grey level intensity profile was fitted for $2\sqrt{Dt}$ using KaleidaGraph 4.5 (Reading, Pa.). The values of 4Dt were then plotted against time to generate a line where the 0.25×slope provided the value of the diffusion coefficient.

Figure 10:
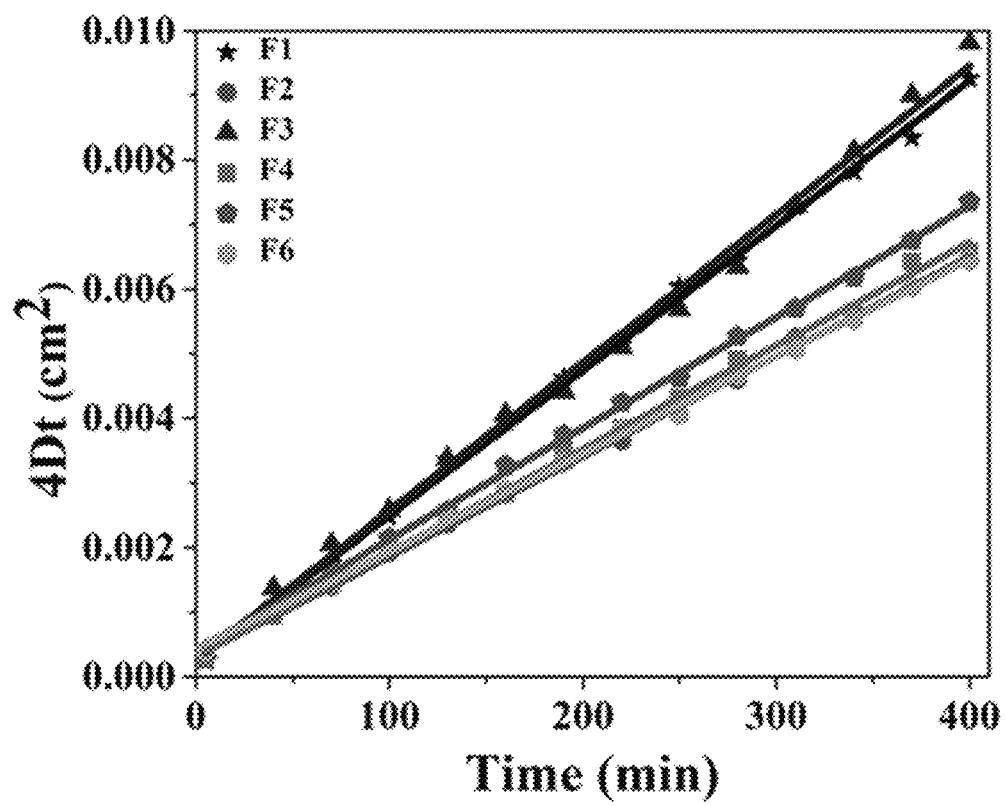
FIG. 10 shows the calculation of diffusion coefficient (D) in the six hydrogel formulations in accordance with embodiments of the present disclosure. At each time point, the value of 4Dt was calculated from a mathematical model of one-dimensional mass transfer fit to an error function, and from the slope of each line D was calculated for each formulation.

The migrating front of the bromothymol dye was observed for 400 min at varying time points (FIG. 3, inset) and then fit to an error function, which approximates one-dimensional mass transfer, at each time point. Values relating the diffusion coefficient (D) to time were plotted resulting in a linear relationship (FIG. 10), which allowed for the determination of the six diffusion coefficients (Table 2). The values for D were found to vary between 6.3×10$^{-8}$ cm$^2$/s to 9.5×10$^{-8}$ cm$^2$/s for the six different hydrogel formulations (Table 2). These findings confirm the mass transfer of water and biomolecules into the thiol-acrylate hydrogels. In the experiments performed here using cancer cell culture, complete medium was added after hydrogel synthesis, which resulted in hydrogel swelling. Similarly, during experimentation, the hydrogels were incubated at 37° C. Both of these conditions can increase the actual value of the diffusion coefficient over the measured value, which can explain how the cells were able to grow and thrive for up to 17 days in the hydrogels. This is evidenced by the presence of viable MDAMB-231 cells of after 17 days in F2 and F4, and also the spheroid formation of MCF 7 cells and an increase in spheroid diameter from Day 0 to Day 12 in F2, F4, and F6.

TABLE 2

Calculated Diffusion Coefficients of Different Thiol-Acrylate Hydrogel Formulations Using Bromothymol Blue (MW 624 g/mol)

| Formulation | Diffusion Coefficient (cm$^2$/s) |
| --- | --- |
| F1 | 9.4 × 10$^{-8}$ |
| F2 | 6.5 × 10$^{-8}$ |
| F3 | 9.5 × 10$^{-8}$ |
| F4 | 6.7 × 10$^{-8}$ |
| F5 | 7.2 × 10$^{-8}$ |
| F6 | 6.3 × 10$^{-8}$ |

Determination of Thiol-Acrylate Hydrogel Degradation

Figure 6:
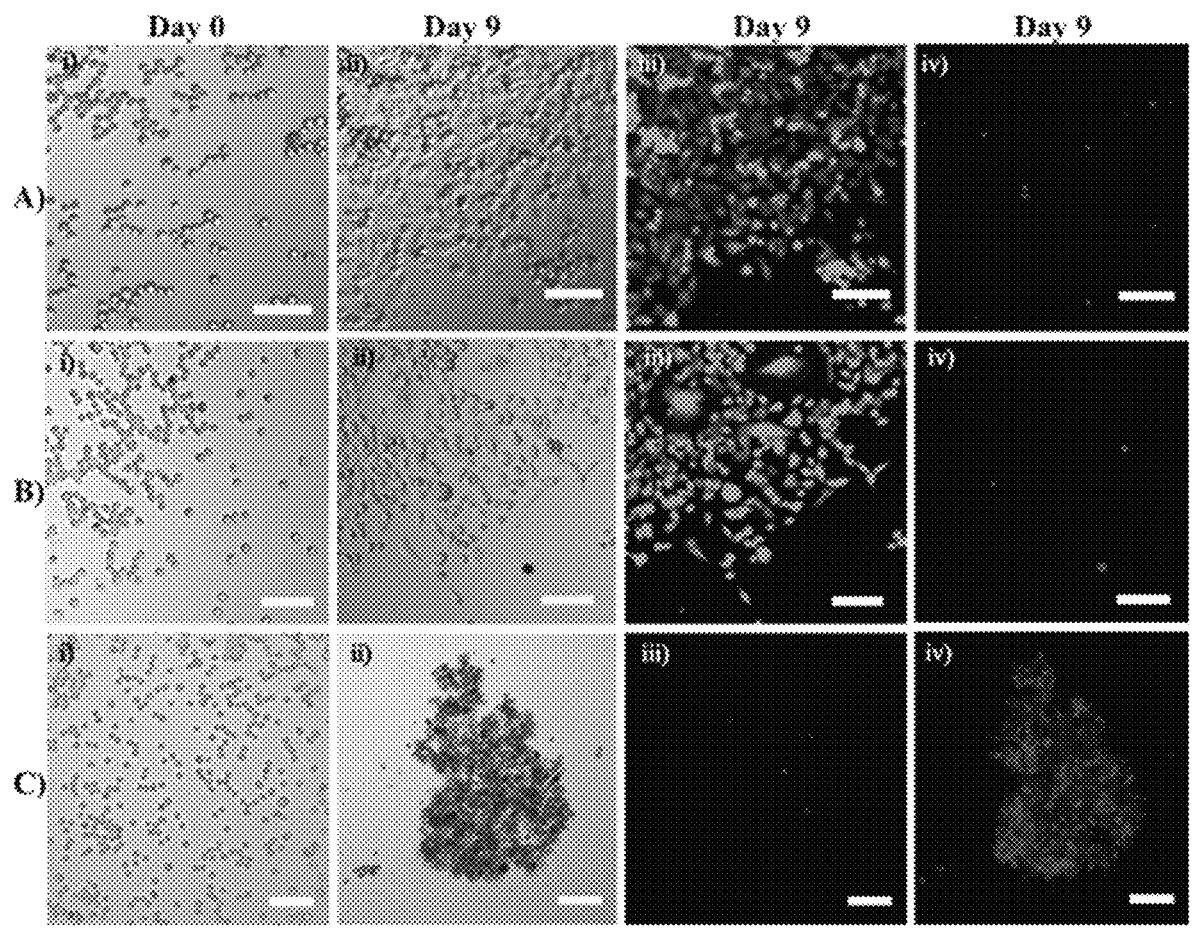
FIG. 6 shows determination of 2D cell adhesion, growth, and viability on thiol-acrylate hydrogels in accordance with embodiments of the present disclosure. MDA-MB-231 cells were seeded onto F2 (A), F4 (B), and F1 (C) and allowed to grow for nine days at 37° C. in complete media. Representative images are shown for initial seeding on day 0 (i) along with brightfield (ii), FITC (iii, live cells), and rhodamine (iv, dead cells) on day 9. Scale bar is 100 μm. Images are representative of duplicate. Images are representative of duplicate experiments.

It has been reported that hydrogel degradation can occur due to ester hydrolysis. To investigate the pH dependence of hydrogel degradation, all six formulations were incubated with either DMEM (the basal media for cell culture, pH 8.05) or PBS (a phosphate buffered solution, pH 7.9) at 37° C. (FIG. 6). Hydrogel degradation was monitored using a gravimetric method. For the degradation study, each hydrogel formulation was synthesized in 8×40 mm glass vials. Once all the hydrogels were solidified, the initial weight ($W_0$) was measured. Then either 500 μL of DMEM (pH 8.05) or PBS (pH 7.9) was added on top of each gel. 1% v/v antibiotic solution (penicillin and streptomycin) was added to the DMEM to prevent bacterial contamination. All samples were maintained at 37° C. and 5% $CO_2$ in a humidified incubator. At the indicated time points, the solution (DMEM or PBS) was carefully removed using a 1 mL micropipette and the gel was weighed ($W_f$). The media was carefully replaced on the gel and returned to the incubator at 37° C. Degradation was monitored from the relative weight percentage of the hydrogel at different time using Eqn. 3:

$$\text{Relative weight percentage of polymer} = \left(\frac{W_f}{W_0} \times 100\%\right) \quad \text{Eqn. 3}$$

Figure 4A:
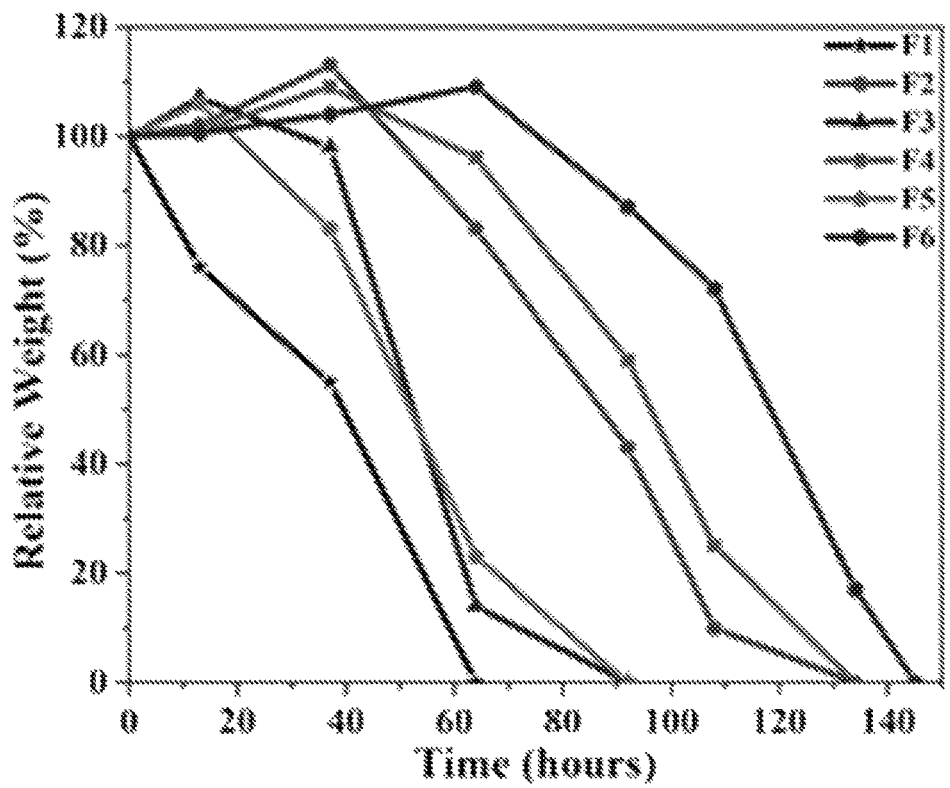
FIGS. 4A-4B show the effect of pH on the degradation of covalently crosslinked thiol-acrylate hydrogels in accordance with embodiments of the present disclosure. All six formulations were incubated with (FIG. 4A) DMEM (pH 8.05) or (FIG. 4B) PBS (pH 7.9) for up to 400 h at 37° C.
Figure 4B:
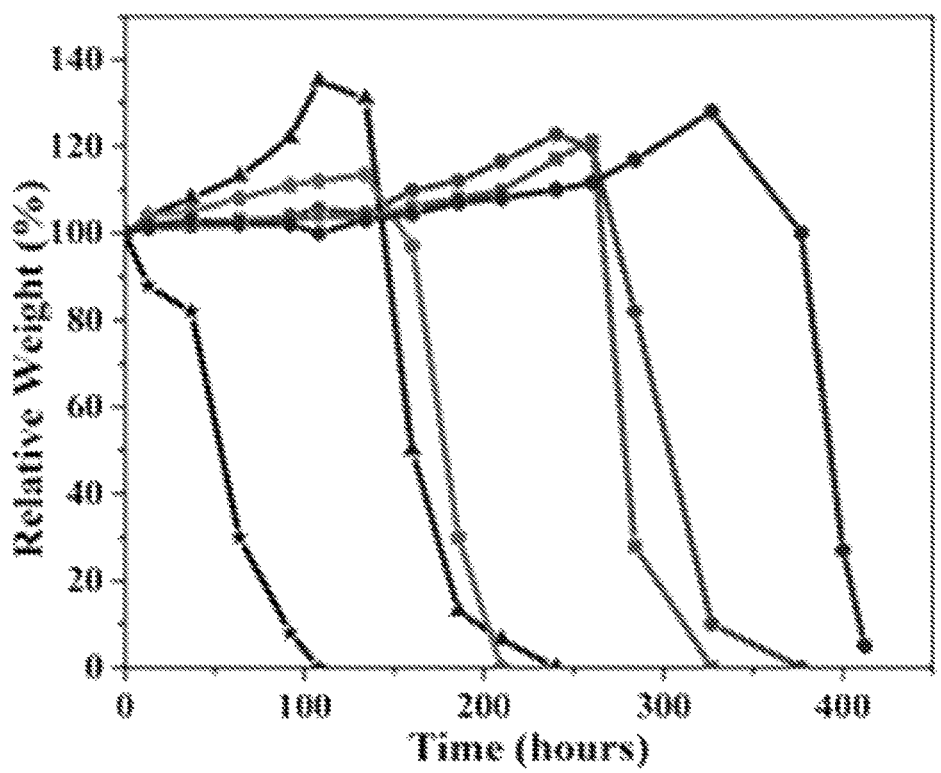

It was observed that formulations F1, F3, and F5 (all with the lower molar ratio of thiol-to-acrylate of 1.0) degraded faster than F2, F4, and F6 (molar ratio of 1.05) in both DMEM (FIG. 4A) and PBS (FIG. 4B). Interestingly, all formulations exhibited greater stability (defined by maintaining the relative weight percent) in PBS with F6 containing ~100% of its initial weight for up to 400 h in PBS compared to 60 h in DMEM (a 6-fold increase in stability). Additionally, the decrease in relative weight was much steeper in hydrogels incubated with PBS compared to those incubated with DMEM. This suggests a slow degradation under cell culture conditions and a fast degradation in salt buffered solutions.

Figure 5A:
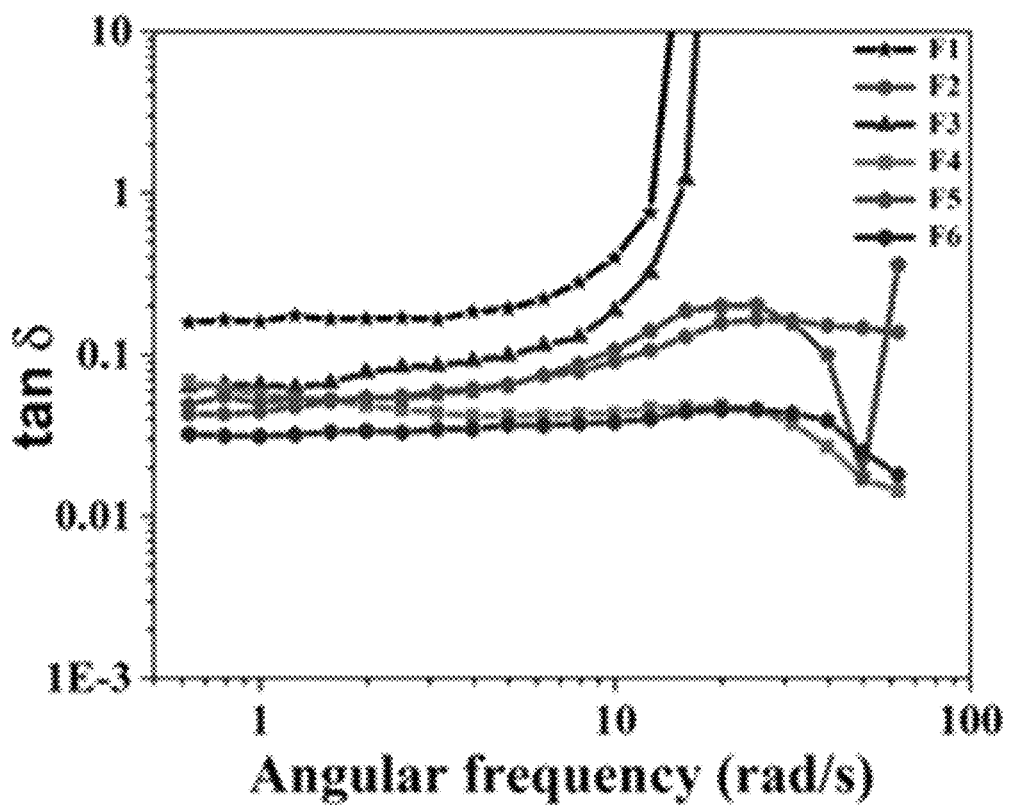
FIGS. 5A-5B show the calculation of rheological properties of six thiol-acrylate hydrogels in accordance with embodiments of the present disclosure. The values for tan δ (FIG. 5A) and the complex shear modulus G* (FIG. 5B) were obtained from the bulk rheology measurements of thiol-acrylate hydrogels taken for a frequency sweep of 0.682 to 62.8 radians/second at 37° C.
Figure 5B:
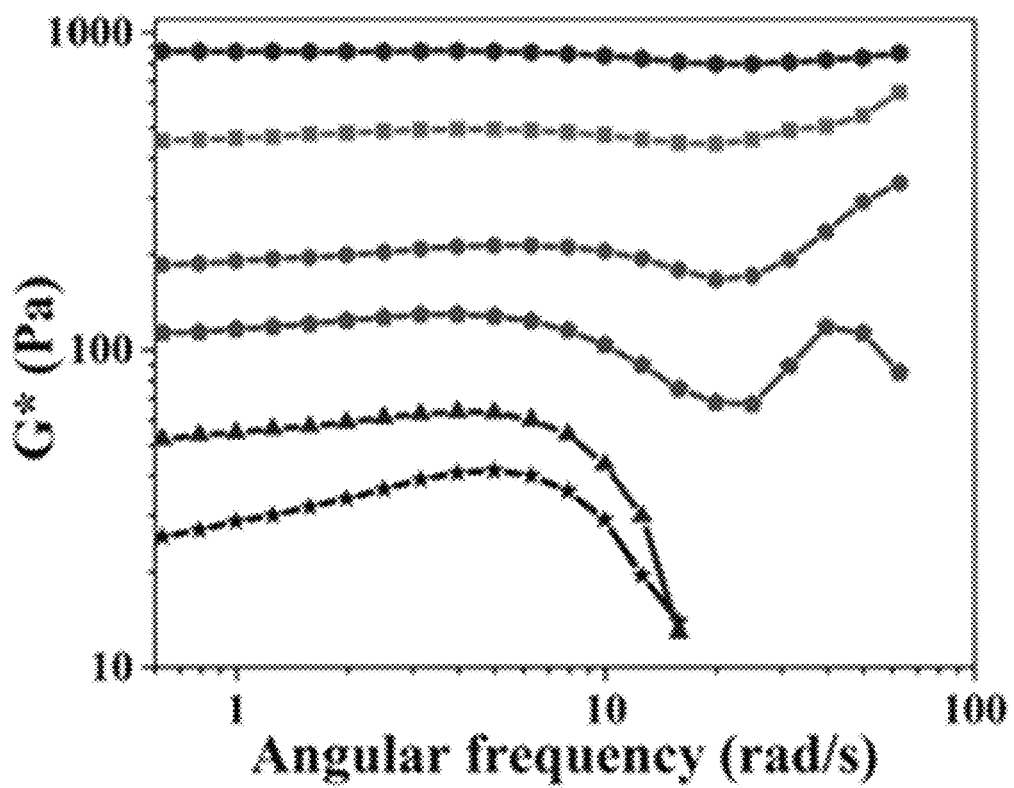
Figure 11A:
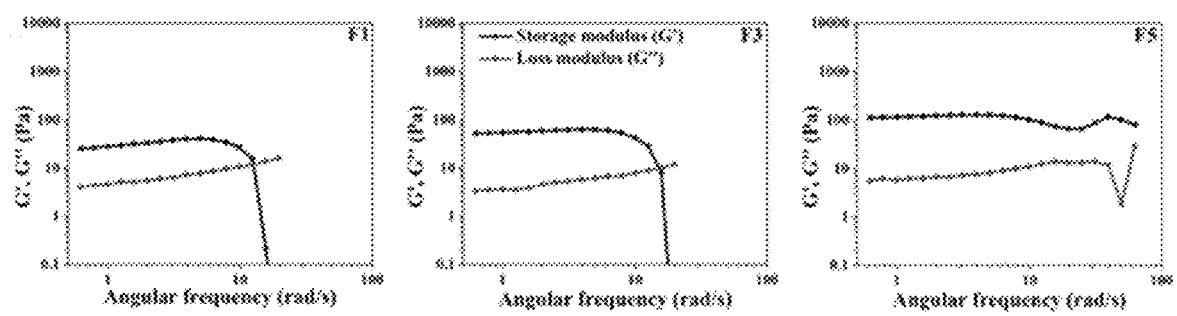
FIGS. 11A-11B show bulk rheology of thiol-acrylate hydrogels in accordance with embodiments of the present disclosure. All measurements were taken during a frequency sweep (0.682 to 62.8 radians/second) of the different formulations at 37° C. G' is the storage modulus (or elasticity of hydrogel).
Figure 11B:
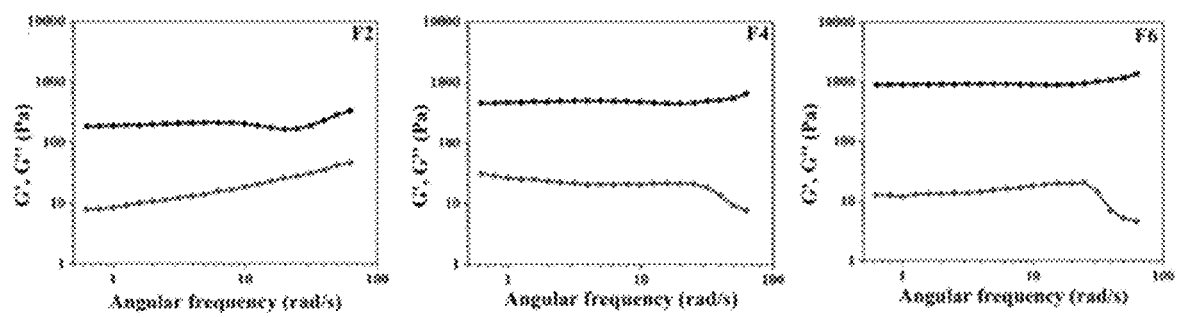

Similar to the findings for gelation time, the monomer weight percentage and molar ratio of thiol to acrylate were also found to modulate the swelling, degradation, and stiffness of the hydrogel. Increasing the monomer content from 8.5 to 9.5 wt % and the molar ratio of thiol to acrylate from 1.0 to 1.05 resulted in higher swelling ratios and longer degradation time (FIGS. 2B and 4A-4B). Due to an increase in the polymer content in the hydrogel, there was an increase in the crosslinking density, which decreased the gelation time and increased the degradation time. This is supported by the fact that the storage modulus (G') is linearly dependent on the crosslinking density of the polymer. The data presented here (FIGS. 5 and 11A-11B) showed a linear increase in G' and G* from F1 to F6, which suggest that crosslinking density increases with increasing polymer weight percentage. This can explain why F6 takes longer to degrade than the other formulations. Changes in hydrogel swelling ratio and degradation time due to increasing the molar ratio of thiol to acrylate from 1.0 to 1.05 can be explained by three possibilities: (a) an increase in polymer crosslink probability, (b) uncrosslinked thiol groups remaining in the hydrogel (FIG. 1b,ii, and (c) potentially impure thiol compounds. A comparison between F1 and F2 (same weight percentage, different molar ratios) shows a greater swelling and decreased degradation in F2. Moreover, F2 exhibits a greater degree of crosslinking than F1 based on a higher value for G' (FIGS. 5 and 11A-11B). These findings indicate that adding a small amount of excess thiol (e.g., increase the molar ratio) maximizes the reaction conversion coupled with some remaining free thiol groups that increase hydrogel mesh size to enhance swelling. The rapid degradation and very low cellular viability in the molar ratio of hydrogels of 1.0 (F1, F3, and F5) indicate that it may be possible that ETTMP is not 100% pure, resulting in a not fully crosslinked hydrogel. This results in a potential remainder of excess acrylate groups that over time decomposes to acrylic acid, which can explain poor cell viability in both the 2D and 3D culture studies (FIGS. 6, 7, and 12) Additionally, incubation of hydrogels in a buffer with a higher pH (DMEM) resulted in a faster degradation time, which can be attributed to increased ester hydrolysis at higher pH values. Therefore, the weight percentage of polymer, molar ratio of thiol-to-acrylate groups, and pH of the media provides control over degradation of the thiol-acrylate hydrogel.

Rheology

Precise control of polymer stiffness is essential for any biological or synthetic hydrogel used for 3D cell culture applications. Numerous studies have shown that the stiffness of the hydrogel can alter cell proliferation and viability. As such, it was important to measure the relative stiffness for all six formulations of the thiol-acrylate hydrogels. Rheology measurements were performed by implementing a small amplitude oscillatory shear using an 8 mm parallel disk geometry at 37° C. for a frequency range of 0.682 to 62.8 radians per second and a constant shear strain amplitude of 10%. The complex shear modulus (G*) value was calculated using Eqn. 4:

$$|G^*| = \sqrt{(G')^2 + (G'')^2} \quad \text{Eqn. 4}$$

G' is the true or shear storage modulus which describes the polymer resistance to deformation and G" is the imaginary modulus, or loss modulus, which provides information about the loss of polymer mechanical energy though dissipation of heat. The stiffnesses of the different hydrogel formulations were compared from the values of G* and the tangent of the phase angle (δ) difference between the applied stress and the deformation (strain). The complex shear modulus |G*| provided insight into the gel stiffness under dynamic conditions. Tan δ was calculated using Eqn. 5:

$$\tan\delta = \frac{G''}{G'} \quad \text{Eqn. 5}$$

If tan δ (0≤tan δ≤1) is around zero, the material is purely elastic but if tan δ is around one or greater than one, then the material is a viscous liquid.

Using bulk rheology, it was found that F6 (with the highest weight percentage of monomers) exhibited the greatest degree of stiffness while F1 was found to be the least stiff hydrogel (FIG. 11A-11B). This was determined by the separation between shear storage modulus (G') and loss modulus (G") resulting in the value of the complex shear modulus (G*) being the highest (and tan δ being the lowest) for F6, which is opposite for F1 (FIG. 6). Similarly, the observed stiffness was found to decrease from F6 to F1 (with decreasing weight percentage of monomer). Increasing the molar ratio of thiols to acrylate groups (1.0 to 1.05) was also found to increase the stiffness of the corresponding hydrogel significantly. This indicates that hydrogel stiffness depends upon both the weight percentage of monomer in the hydrogel as well as the molar ratio of thiol to acrylate, with a greater amount of thiol providing a stiffer hydrogel (comparing F2 to F1).

Example 4: Visualization of Exemplary Hydrogels

2D Visualization of Cell Adhesion, Proliferation, and Viability

Once all of the chemical and physical properties of the thiol-acrylate hydrogels were determined, the next step was to evaluate how they functioned as a scaffold to support cancer cell proliferation. Initial assessment of the cytotoxicity of the thiol-acrylate hydrogels was performed using a 2D cell culture approach to eliminate any questions regarding mass transfer of nutrients into the hydrogel. 100 µL of each hydrogel formulation was added to wells of a 96 well plate (Corning). After the hydrogel solidified, 100 µL of a suspension of MDA-MB-231 cells ($2.5 \times 10^4$ cells/mL) in complete media was added on top of the hydrogel. Cells were cultured at 37° C. with 5% $CO_2$ in a humidified incubator for nine days. To ensure sufficient nutrients, complete media was replenished every two days. Cell viability was determined after nine days of culture using the live cell stain Calcein AM (Life Technologies) and the dead cell stain ethidium homodimer-1 (EthD-1, Life Technologies) at concentrations of 3.5 µM and 3.85 µM, respectively, in extracellular buffer (ECB). At day nine, the media was removed from each well followed by immediate addition of 100 µL of staining solution, which was incubated with the cells for 70 min in the dark followed by visualization using fluorescent microscopy. Cellular fluorescence was visualized using a Leica DMi8 inverted microscope outfitted with a FITC filter cube, 20× objective (Leica HC PL FL L, 0.4× correction), and phase contrast and brightfield applications. Digital images were acquired using the Flash 4.0 high speed camera (Hamamatsu) with a fixed exposure time of 35 ms for the FITC filter (green, live cells), 55 ms for the rhodamine filter (red, dead cells), and 10 ms for brightfield. Image acquisition was controlled using the Leica Application Suite software. All images were recorded by using the same parameters. A control experiment was performed using 3 wt % agarose (in DI water) gel instead of the thiol-acrylate hydrogels. For this experiment, 100 µL of warm agarose was added to the 96 well plate followed by the same method described above.

Initial assessment of the cytotoxicity of the thiol-acrylate hydrogels was performed using a 2D cell culture approach to eliminate any questions regarding mass transfer of nutrients into the hydrogel. Triple-negative breast cancer cells (MDA-MB-231), model cancer cell line, were seeded on top of all six hydrogel formulations and allowed to adhere and grow for nine days at 37° C. followed by a terminal viability stain (FIG. 6). A relationship between cell attachment (and proliferation) and molar ratio of thiol to acrylate groups was observed. All three formulations with the 1.05 molar ratio (F2, F4, and F6) supported the attachment and proliferation of the cancer cells (FIG. 6). Analysis of the cells found that 95-97% of cells were viable on F2, F4, and F6. Conversely, the cancer cells were unable to adhere to the surface for all three formulations with the 1.0 molar ratio (F1, F3, and F5) resulting in an aggregate suspension of cells above the surface of the hydrogel. The majority of the cells incubated with F1, F3, and F5 were also found to not be viable after nine days of culture with ~1-5% viable cells remaining (FIG. 6). This suggests that the 1.0 molar ratio of thiol to acrylate not only prevented attachment, but also was cytotoxic. To ensure it was the thiol-acrylate hydrogel that resulted in cell death rather than the method, a control 2D proliferation experiment was performed using agarose as the basement hydrogel. As expected, the cells were not able to adhere to the agarose, but were found to be viable after nine days of culture, further confirming that the formulations with the 1.0 molar ratio of thiol to acrylate (F1, F3, and F5) were cytotoxic.

This suggests that the thiol-acrylate hydrogels with the 1.05 molar ratio of thiols to acrylates is compatible with cell spreading and that cancer cells can release their own extracellular matrix (ECM) components on the hydrogels to facilitate proliferation. Finally, there was no observable difference in cell viability or proliferation in the different weight percentage formulations.

Figure 8:
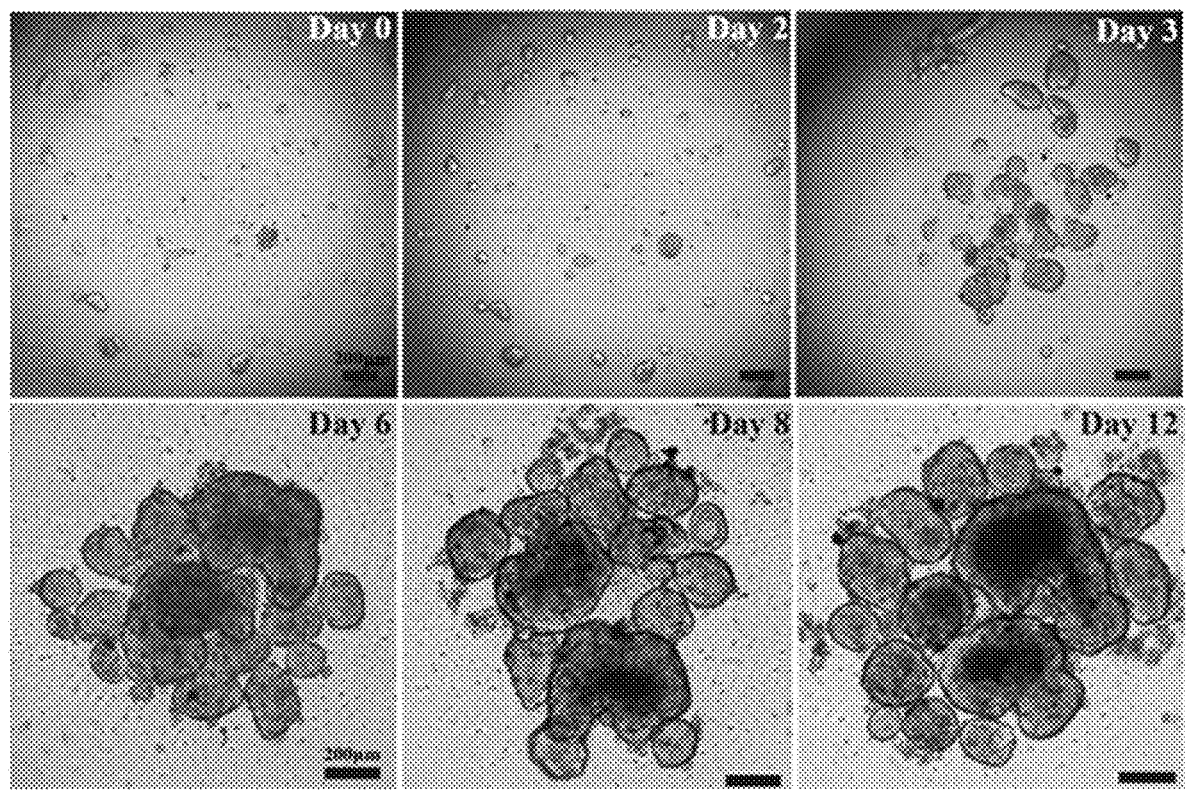
FIG. 8 shows evaluation of 3D spheroid formation of MCF7 cells within thiol-acrylate hydrogels in accordance with embodiments of the present disclosure. MCF7 cells were seeded into F2 and allowed to grow for 12 days at 37° C. in complete media within the thiol-acrylate hydrogels. Representative bright field images are shown for initial seeding on day 0 and their growth over time on days 2, 3, 6, 8 and 12. Scale bar is 200 μm in all images. Images are representative of duplicate experiments.

Results from the studies presented herein confirm that the three formulations using the molar ratio of thiol to acrylate of 1.05 were noncytotoxic and capable of supporting cellular adhesion and growth while maintaining sufficient viability both two dimensionally and three dimensionally. This is supported by the observation of very little cell death of MDA-MB-231 cells grown in 3D (FIGS. 6 and 13) and the formation and growth of a significant number of MCF7 3D spheroids (FIGS. 8 and 14) in the formulations with the excess thiol (F2, F4, and F6). All these findings indicate that for 3D cell culture in these types of gels, two factors affect cellular growth: the molar ratio of thiol to acrylate and weight percentage of polymer in hydrogel formulation.

3D Visualization of Cell Proliferation and Viability

Proliferation and viability of cancer cells in the thiol-acrylate hydrogels grown under 3D conditions were assessed. MDA-MB-231 cells were detached from the T-75 flasks and centrifuged at 1800 rpm for 2.5 min as described previously. The supernatant was removed and the cell pellet was resuspended in the pre-mixed thiol-acrylate hydrogel to a final volume of 1 mL with a final cell density of $5 \times 10^4$ cells/mL. All six hydrogel formulations were prepared as described above with the vortex step occurring prior to the addition of the cells to avoid cellular shearing. The cell/hydrogel suspension was mixed gently using a micropipette to ensure a homogeneous distribution of cells within the hydrogel. An advantage of the thiol-acrylate hydrogel is that the time-dependent gelation by the base catalyzed Michael addition allows for manipulation and transfer of the suspension for ~2-8 min to facilitate the transfer of the suspension to cell culture plates. 100 µL of the cell/hydrogel suspension was transferred to each well of a 96-well plate specifically designed for the growth of 3D spheroids (Corning 4515). Once the gel solidified, 100 µL of cell culture media was added to each well and the cells were incubated as described previously. The growth media was replenished every two days to ensure proper nutrient levels. Assessment of cellular viability was performed as described above on days 4, 7, 11, and 17. The number of live and dead cells were calculated using a custom Python code called FluoroCellTrack. MCF-7 was seeded into TA hydrogels with excess thiol (F2, F4, and F6) as described earlier for MDA-MB-231 cells with a cell density of $1 \times 105$ cells/ml. Brightfield images were acquired every 24 hr to evaluate spheroid formation and their growth.

Figure 7:
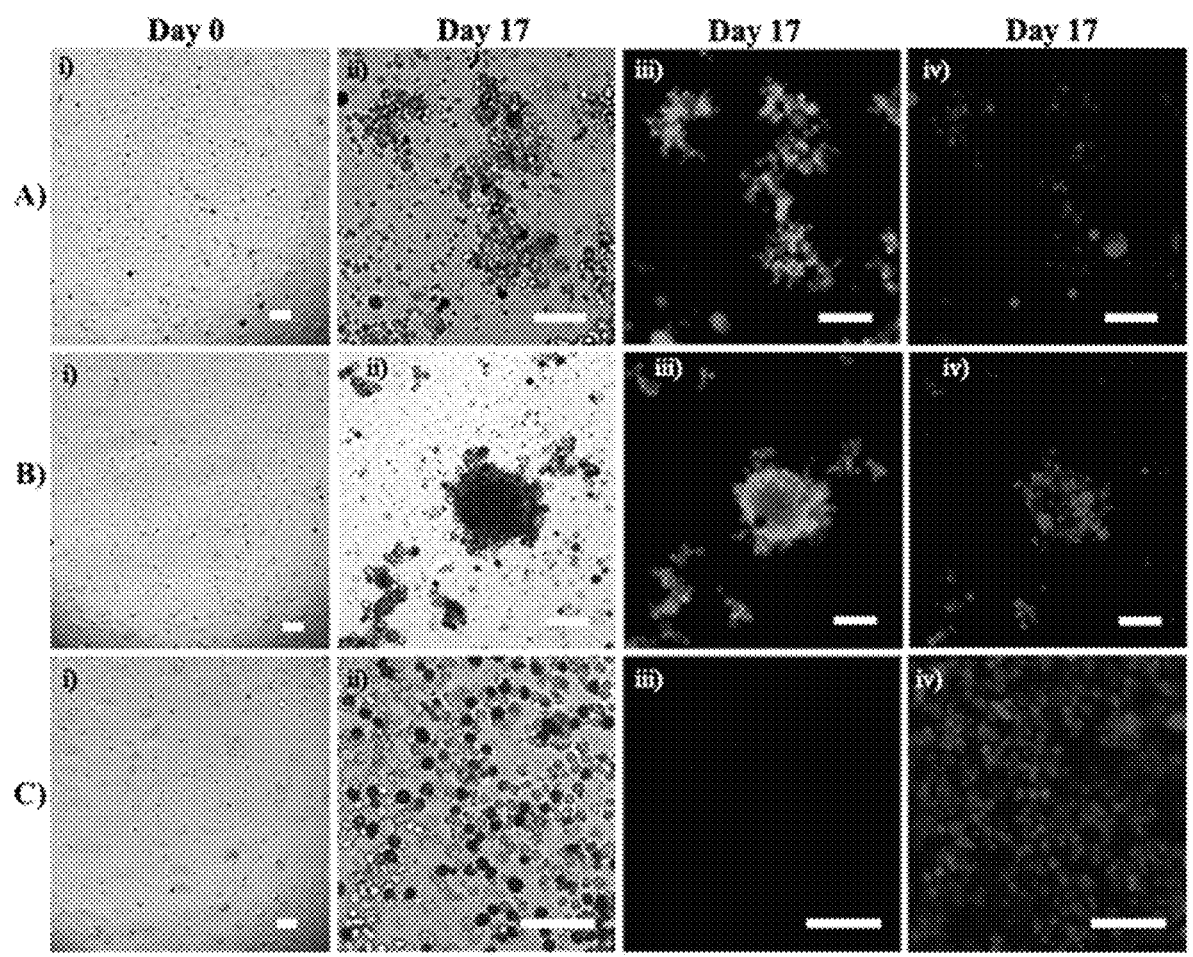
FIG. 7 shows evaluation of 3D proliferation and viability of MDA-MB-231 cells within thiol-acrylate hydrogels in accordance with embodiments of the present disclosure. MDA-MB-231 cells were seeded into F2 (A), F4 (B), and F1 (C) and allowed to grow for 17 days at 37° C. in complete media within the thiol-acrylate hydrogels. Representative images are shown for initial seeding on day 0 (i) along with brightfield (ii), FITC (iii, live cells), and rhodamine (iv, dead cells) on day 9. Scale bar is 100 μm. Images are representative of triplicate experiments.
Figure 12:
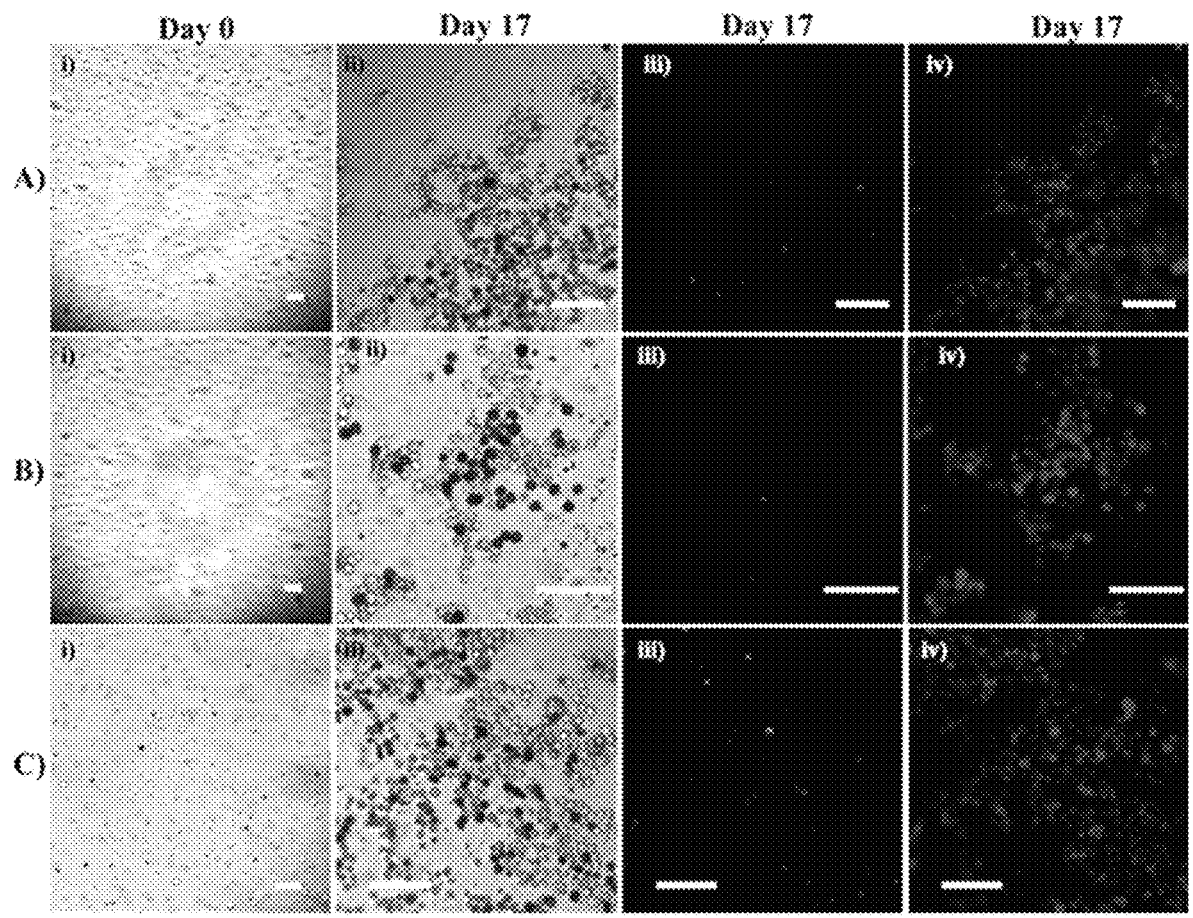
FIG. 12 shows evaluation of 3D growth and viability of MDA-MB-231 cells within thiol-acrylate hydrogels in accordance with embodiments of the present disclosure. MDA-MB-231 cells were seeded into F3 (row A), F5 (row B), and F6 (row C) and allowed to grow for 17 days at 37° C. in complete media within the thiol-acrylate hydrogels. Representative images are shown for initial seeding on day 0 (i) along with brightfield (ii), FITC (iii, live cells), and rhodamine (iv, dead cells) on day 9. Scale bar is 100 μm. Images are representative of triplicate experiments.
Figure 13:
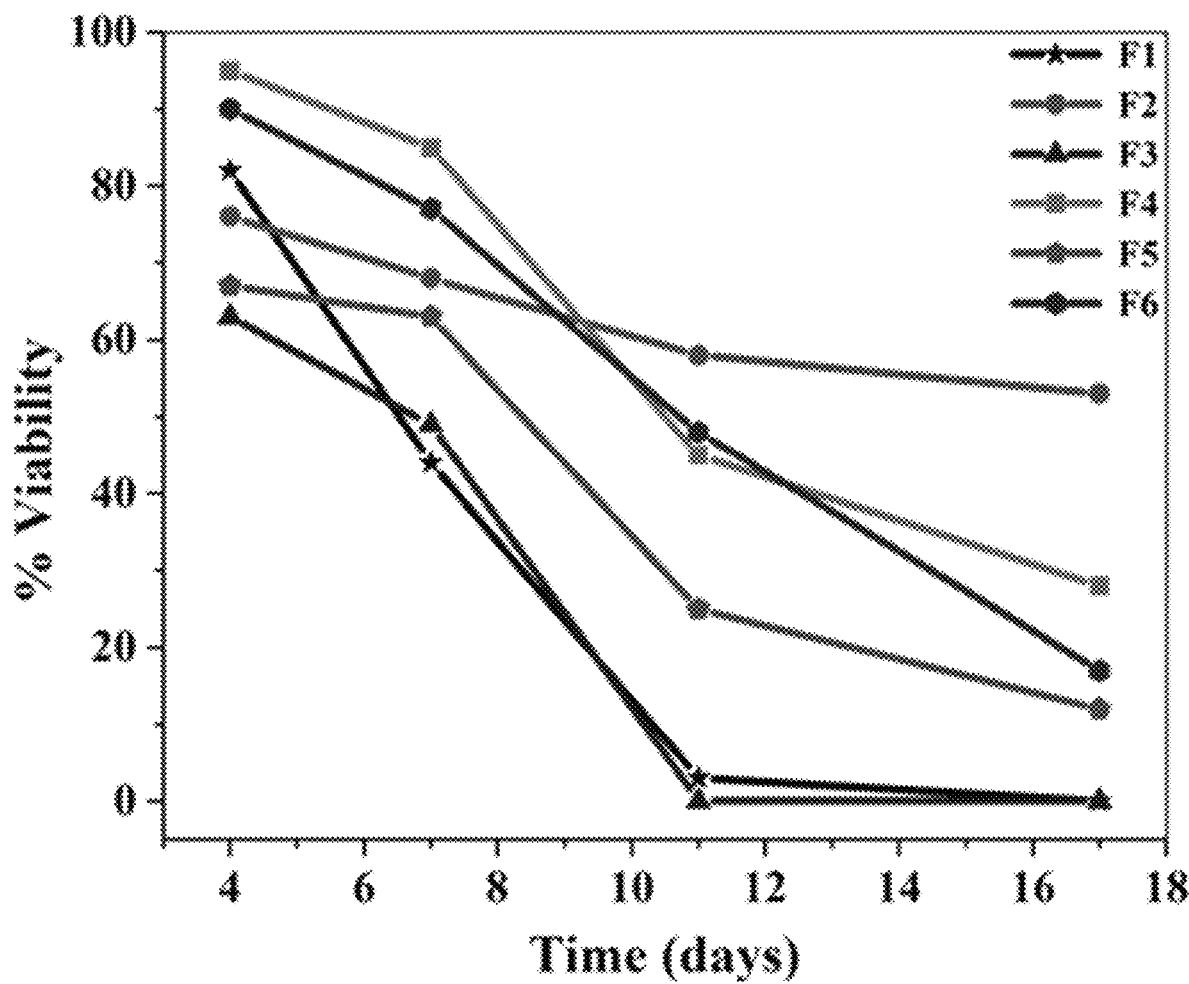
FIG. 13 shows quantification of cell viability in thiol-acrylate hydrogels in accordance with embodiments of the present disclosure. The number of live and dead MDA-MB-231 cells were assessed during the 17-day culture within the thiol-acrylate hydrogels using an automated Python algorithm. A minimum of 175 cells were counted for each formulation at each of the days that viability was assessed (days 4, 7, 11, and 17).
Figure 14:
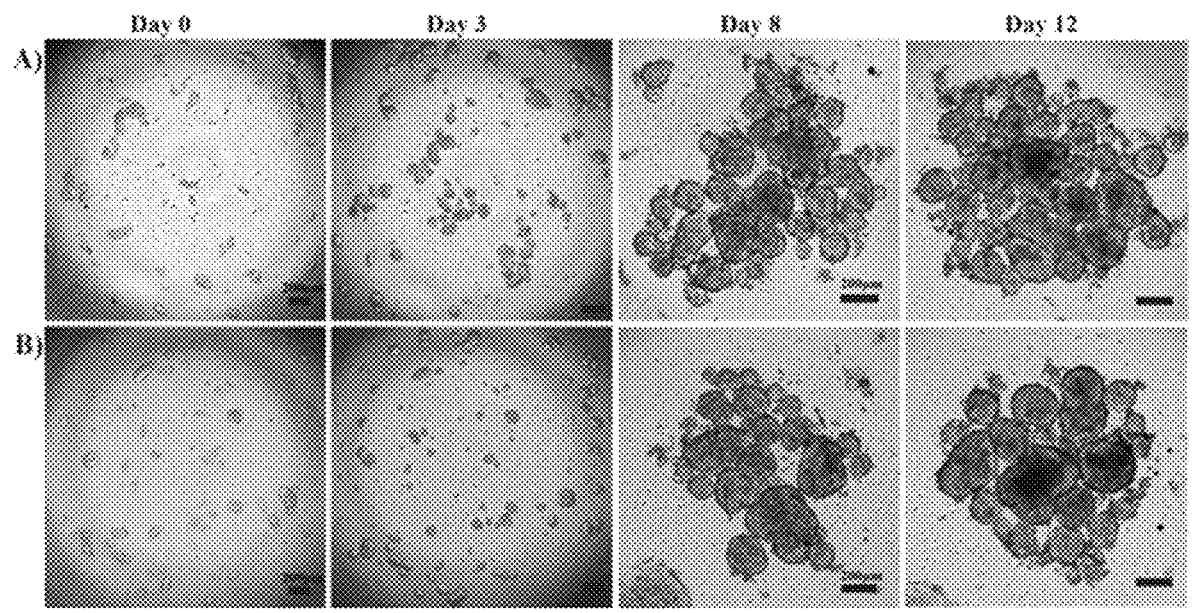
FIG. 14 shows evaluation of 3D spheroid formation of MCF7 cells within thiol-acrylate hydrogels in accordance with embodiments of the present disclosure. MCF-7 cells were seeded into F4 (A) and F6 (B) and allowed to grow for 12 days at 37° C. in complete media within the thiol-acrylate hydrogels. Representative bright field images are shown for initial seeding on day 0 and their growth over time in day 3, 8 and 12. Scale bar is 200 µm. Images are representative of duplicate experiments.

Here, MDA-MB-231 cells were immediately seeded into all six formulations of the thiol-acrylate hydrogel and allowed to grow for 17 days in a custom spheroid 96-well plate at 37° C. The findings from this experiment were similar to what was discovered with the 2D proliferation studies; however, the weight percentage of the monomers in the hydrogel influenced growth and proliferation Cells seeded within the formulations with the 1.05 molar ratio of thiol to acrylate and the lower weight percentages (F2: 8.5% and F4: 9%) were observed to grow and remain viable after 17 days of culture (FIG. 7). Moreover, in F2 and F4 the cells formed into the aggregates with a mix of alive and dead cells. Interestingly, the highest weight percentage (9.5%) formulation using the 1.05 molar ratio (F6) exhibited the lowest overall viability after 17 days (FIG. 7) suggesting that higher monomer content, corresponding to the stiffest hydrogel, did not provide optimal 3D cellular growth conditions. Similarly to what was observed in the 2D proliferation studies, none of the 1.0 molar ratio formulations (F1, F3, and F5) were able to sustain cellular growth under 3D cell culture conditions (FIGS. 7 and 12). To quantify the number of viable cells in all six formulations, the microscopy data was processed by an automated Python algorithm capable of identifying and counting fluorescent cells using different channels (e.g., green for live and red for dead). The number of viable cells observed in all six formulations throughout the 17-day time course is consistent with the microscopy data presented in FIG. 7. To quantify the number of viable cells in all six formulations, the microscopy data were processed by an automated Python algorithm capable of identifying and counting fluorescent cells using different channels (e.g., green for live and red for dead). FIG. 13 summarizes the number of viable cells observed in all six formulations throughout the 17-day time course, which is consistent with the microscopy data presented in FIGS. 7 and 12. Additionally, it was observed that cancer cells that were seeded closer to each other on day 0 were more likely to survive in F2 and F4 due to their ability to communication with nearby cells and eventually form aggregates. MCF7 spheroids growing on a hydrogel disclosed herein can be seen in FIG. 15. Conversely, single isolated cancer cells were more likely to be non-proliferative and dead by the end of the 17-day period.

The results from the MDA-MB-231 studies above confirmed the growth and viability of cancer cells in the TA hydrogels; however, this cell line has been shown in the literature to be resistant to form 3D spheroids and is normally referred to as cellular aggregates instead of cellular spheroids. To study this phenomenon, MCF7 breast cancer cells were used to investigate the potential for the TA hydrogel to support 3D spheroid formation. This cell line has been well documented to form 3D spheroids using a number of methods and materials. MCF7 cells were seeded in the three formulations with a higher thiol-to-acrylate ratio (F2, F4, and F6), which demonstrated the best viability with the MDA-MB-231 cells. The cells were incubated for 12 days at 37° C. to observe 3D spheroid formation. It was observed that all three formulations supported the formation and growth of 3D spheroid of ~20-25 spheroids per well (FIG. 8). 3D spheroids started to form by Day 2 in F2 and by Day 3 in F4 and F6. The diameter of the spheroids increased with time during the 12-day incubation, indicating significant cellular growth. After 12 days of culturing, 3D spheroids with diameters ranging from 100 to 600 μm were observed. Additionally, the 3D spheroids were observed to aggregate in the center of the well during the 12-day incubation due to the time-dependent degradation of the TA hydrogel.

Example 5: Microfluidic Device Preparation and Viability Studies

Microfluidic devices have become a tool to rapidly generate 3D spheroids. A popular approach utilizes microwell arrays that have been modified to prevent cellular attachment and force cellular aggregation into 3D spheroids. These devices can rapidly generate a large number of spheroids; however, most microwell arrays cannot facilitate on-chip interrogation of 3D spheroids and suffer from disaggregation due to fluid shear stress. Similarly, the spheroids generated in the above methods suffer from significant heterogeneity since they are generated from hundreds to thousands of different cells. Described herein are methods and systems incorporate the thiol-acrylate (TA) hydrogel scaffolds described above into a microfluidic droplet trapping array to generate and study 3D spheroids.

Three different trapping arrays were fabricated with 70, 150, or 300 μm circular traps to study the effect of droplet size and cell seeding density on spheroid formation and growth in the TA hydrogel scaffold. The 70, 150, and 300 μm trapping array consisted of 785, 990, and 450 traps respectively, and was capable of ~99% droplet trapping and ~90% cellular encapsulation. The TA hydrogel allowed for rapid (~30-40 min) polymerization of the scaffold followed by removal of the oil phase and replacement with complete media to initiate spheroid growth. The growth and viability of model breast cancer spheroids using MCF7 at 37° C. was confirmed for up to four days under static conditions and longer with continuous infusion of fresh growth media. This study also identified that a minimum number of encapsulated cells (~4-6) are needed to generate a spheroid and that single encapsulated cells are less likely to grow into a full-blown spheroid. The findings from this study highlight an alternative approach to generate 3D spheroids incorporating an easy-to-use, inexpensive scaffold that can be used for high-throughput drug screening.

Device Preparation

The device described herein includes a flat layer having two inlets and an outlet. The flat layer is above a bottom PDMS device layer that includes microfluidic flow channels and a trapping array, such the that the trapping array is provided below the flow channels (FIG. 15).

The PDMS layer, or device replica, can be formed from a silicon master. Silicon wafers for different trapping sizes were developed using standard soft lithography. In some aspects, the wafers are about 4 inch wafers. Briefly, AutoCAD (2015 version, AutoDesk) was used to create geometries for the microchannels which were printed onto iron oxide/chrome masks (Front Range). A silicon master was fabricated using a two-step lithography process to generate the bottom fluidic layer and top trapping array. SU-8 2025 (MicroChem) was spun onto a clean 4" silicon wafer (University Wafer) using a spin coater (WS-650 Series Spin Processor, Laurell Technologies Corp) at 3000 rpm for 30 s to achieve a thickness of 40 μm for the bottom fluidic layer. The wafer was pre-baked at 65° C. for 5 min and then baked at 95° C. for 25 min followed by a gradual cooldown to 25° C. UV exposure was performed in a custom-built UV exposure system with a Blak-Ray B-100 series UV lamp (UVP, LLC) with 1 mW/cm$^2$ power intensity for 60 s. A post exposure bake was performed at 65° C. for 5 min and at 95° C. for 25 min. A second 40 μm layer of SU-8 2025 was spun onto the wafer to generate the overhead trapping array followed by the same pre-exposure bake, UV exposure, and post-exposure bake steps. Following the second post exposure bake step, the wafer was immersed in an SU-8 developer solution (MicroChem) for ~5 min followed by a rinse with isopropyl alcohol (VWR) to remove all uncrosslinked SU-8. The wafer was dried with compressed nitrogen and then hard baked at 150° C. for 30 min to stabilize the patterns.

To make the Polydimethylsiloxane (PDMS) device replica, a base and curing agent were mixed in a ratio of 10:1 and degassed under vacuum for 45 minutes before pouring it on a silicon wafer. Similarly, to obtain a flat PDMS layer 20 g of degassed PDMS mixture (having the same ratio of base and curing agent as before) poured on a 100 mm petri dish and placed it on a hot plate at 65° C. for 12 hours to cure completely. The PDMS replica and flat layer were carefully removed from the wafer and petri dish before cutting them in proper sizes using the X-Acto knife. The PDMS flat layer and device replica were aligned visually to make holes from the flat layer side at two inlets and outlet using a blunted 18-gauge needle. Later, those holes were blown with high-pressure nitrogen to remove any unwanted tiny PDMS pieces that were stuck inside the inlets and outlet holes. Both layers of PDMS were thoroughly cleaned using scotch tape before binding them using a plasma binder. The plasma binder was vacuumed for 2 minutes and 30 seconds before treating the PDMS layers with plasma for 55 seconds. Finally, both the PDMS device replica and flat layer were aligned visually and left in a petri dish at room temperature overnight to develop strong interaction between these two layers. The surface inside the device was made hydrophobic by treating the inside of the device with aquapel and excess aquapel was removed by flowing high-pressure nitrogen gas and Novec 7500 oil through the device.

Working Principle of Droplet Generator

The device was wiped with a chem wipe socked with 70% (v/v) ethanol solution and once dried, it was placed on a sterile 100×20 mm petri dish. Six 16-inch-long microfluidic tubes were cut and autoclaved before using them in a different stage of the on-chip experiment. The droplet generator used in this system has two inlets: one is used to inject oil and surfactant mixture and the other inlet is used to inject hydrogel mixed with cells (FIG. 2A) into the device. Before starting, the droplet generation air inside the device was removed by flowing Novec 7500 oil containing 0.5% (w/w) Fluoro-surfactant at a flow rate of 1000 µL/h. While air from the device was removed, MCF-7 cells were centrifuged at 300 g for 6 minutes to obtain a cell pellet. In the meantime, 8.5 wt. % thiol acrylate (TA) hydrogel was made in Dulbecco's Modified Eagle Medium (DMEM) media (containing 1% v/v penicillin-streptomycin) as previously described. Both hydrogel and the test tube containing cells were brought under a biosafety hood. The cell pellet was mixed with 1 mL of liquid hydrogel mixture using a 1 mL micropipette and transferred into a 1 mL sterile syringe connected with a 23-gauge needle underneath the biosafety hood. To make hydrogel droplets, both oil containing 0.5% (w/w) fluorosurfactant and hydrogel were flowed at a specific flow rate (Table 3) using two Harvard syringe pumps which generate droplets at the flow-focusing junction of the device (FIG. 16A).

Due to the oil flow, generated droplets are carried out to the trapping array and trapped into the traps (FIG. 16B). Once all the traps were filled with droplets, droplet generation was turned off and any extra droplet from the trapping was flushed away from the device using oil flow (1000 uL/h). Followed by the removal of extra droplets, the syringe was swapped with a syringe containing only Novec 7500 oil. The oil was flowed at a rate of 500 uL/h for one hour before introducing media into the device to remove surfactant from the device, as the presence of surfactant negatively effects later steps such as removal of oil from the device using media flow. During this one-hour waiting period, the Michael addition reaction between thiolate and acrylate was performed and resulted in fully crosslinking hydrogel. During the completion of gelation, the whole device was submerged beneath autoclaved deionized (DI) water containing 1% (v/v) penicillin-streptomycin to prevent droplets from shrinking due to water evaporation and to prevent air from entering the device. The media was introduced and flowed through the device at a rate of 500 uL/h for 30 minutes, then the whole device was imaged at 5× magnification under a Leica DMi8 inverted microscope.

Figures 17A, 17B, 17C:
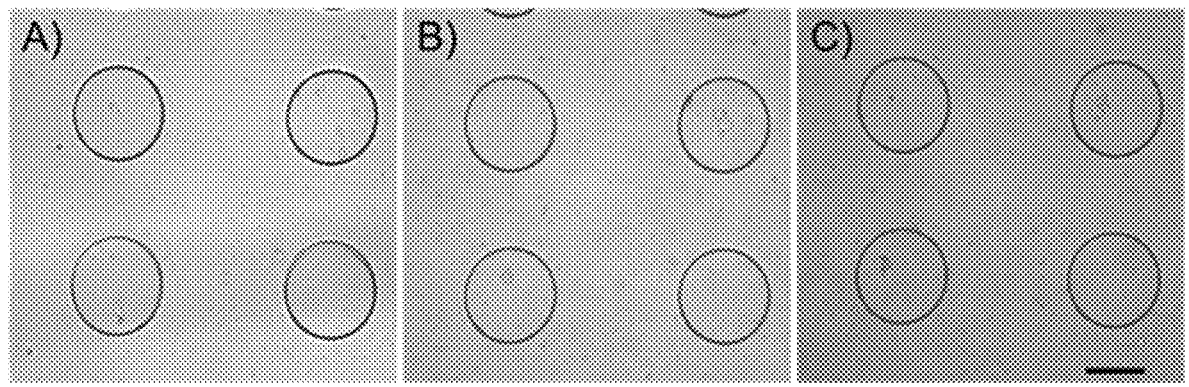
FIGS. 17A-17C show generation of MCF-7 spheroid and changes of their morphology over time in absence of contentious media flow through a device in accordance with embodiments of the present disclosure. Brightfield images of trapping array in day 0 (FIG. 17A), day 2 (FIG. 17B), and day 6 (FIG. 17C) taken in 10× magnification under Leica microscope. The scale bar is 200 µm.

Finally, the water used to submerge the device was removed using a 25 mL pipet. DMEM media containing 1% (v/v) penicillin-streptomycin was added into the petri dish. While the device was submerged underneath the DMEM media, all three microfluidic tubings (inlets and outlet) were carefully removed, and the petri dish was covered with a lid before placing it inside the 37° C. incubator. The media was replaced every two days. However, from several trials, it was observed that beyond day two spheroids were not growing inside the device (FIGS. 17A-17C). To solve this issue, gravity-driven media flow through the device (below) was introduced for continuous nutrient flow and waste removal from the device.

Incorporation of Gravity-Driven Media Flow to Maintain Cells Inside the Device

Figure 18:
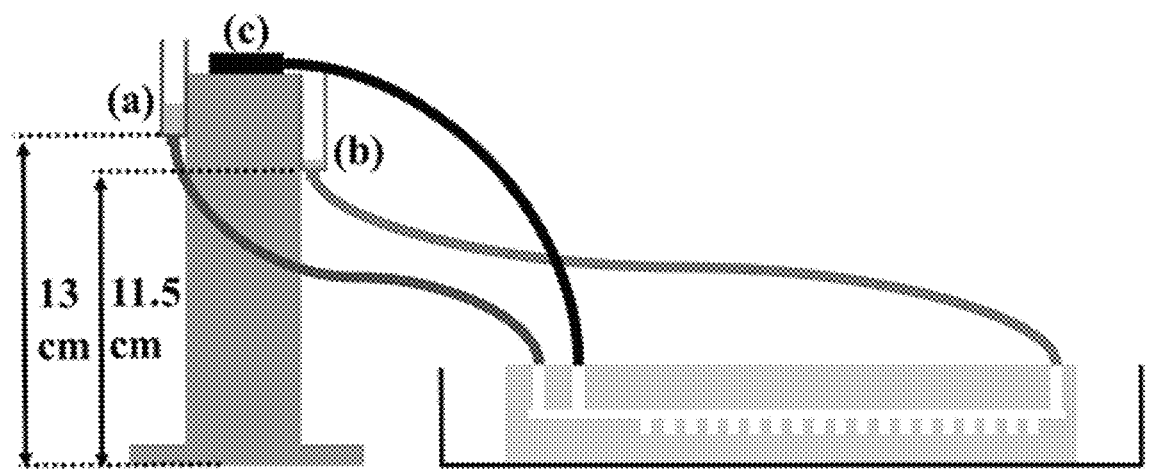
FIG. 18 shows a schematic representation of a gravity-driven media flow setup for the microfluidic droplet generator device in accordance with embodiments of the present disclosure. 5.0 mL plastic syringes were used as a reservoir (a) and collector (b). A closed 1.0 mL glass syringe (c) was used to close the aqueous port of the device.
Figure 19:
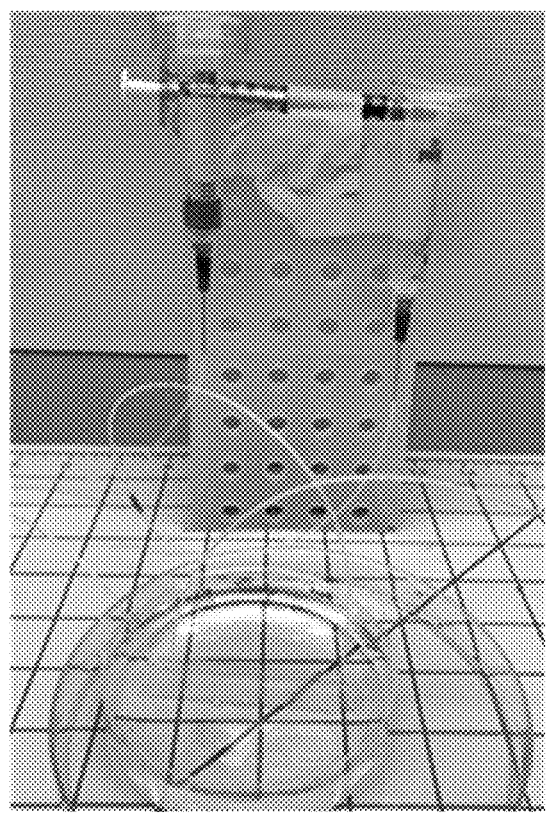
FIG. 19 shows a representation of gravity-driven media flow setup in an on-chip experiment in accordance with embodiments of the present disclosure.
Figure 20A:
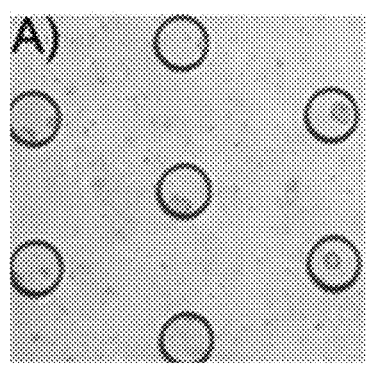
FIGS. 20A-20E show on-chip viability of MCF-7 spheroids which was cultured on-chip for nine days before carried out live and dead staining in accordance with embodiments of the present disclosure. Representative images are shown for brightfield images of trapping array in day 2 (FIG. 20A) and day 9 (FIG. 20B). FITC (FIG. 20C, green indicates live cells), rhodamine (FIG. 20D, red indicates dead cells), and an overlay image (FIG. 20E) on day 9. The scale bar is 150 µm.
Figure 20B:
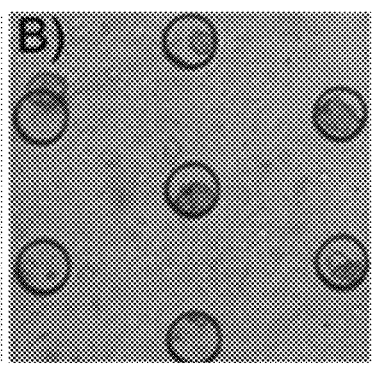
Figure 20C:
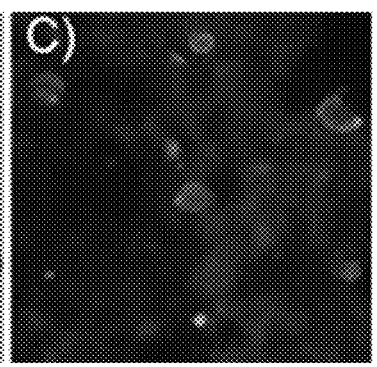
Figure 20D:
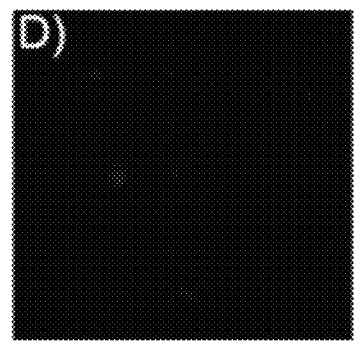
Figure 20E:
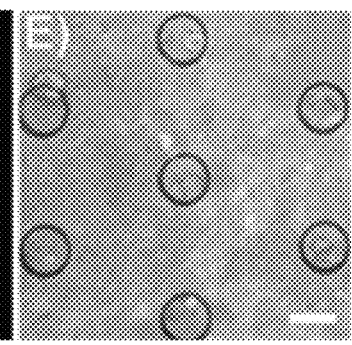

Continuous nutrient flow to the cells is very important for cells to survive and to multiply. This continuous media flow can be provided using syringe pumps. However, syringe pumps are expensive, hard to move from one place to another, and difficult to fit inside a $CO_2$ incubator due to space limitations. Finally, in the syringe pump setup, it is difficult to swap a new syringe with the old one without introducing air inside the device. However, with the gravity-driven flow, most of these problems can be solved. To develop this system, a single block of test-tube holders was used as a stand to hold both the reservoir and collector at a height of 13 and 11.5 cm, respectively. Both the reservoir and collector were made of 5.0 mL BD plastic syringes and a 23-gauge needle was used to connect the microfluidic tubing with the syringes. Microfluidic tubing from the reservoir was connected to the oil port of the device, which helped media to flow through the device due to pressure difference between the reservoir and collector. Finally, the media exited through the outlet port, which was connected to the collector by another piece of microfluidic tubing. To prevent any media leakage through the aqueous port, it was closed by connecting a closed syringe using microfluidic tubing. For cell culture purposes, media was replenished every 24 hours by adding 4 mL media into the reservoir and at the same time removing 3 mL from the collector (FIGS. 18 and 19).

The amount of media in the reservoir and space between the reservoir and collector effects the resultant flow rate and can be adjusted on the device according to need. The ratio of fluidic layer depth and trap height can be tuned to prevent

TABLE 3

Droplet generator parameters tested for spheroid growth

| Trap diameter (µm) | Trap height (µm) | Fluidic layer height (µm) | Cell seeding density (million cells/mL) | Experimental length (Days) | To get appropriate droplet size | |
|---|---|---|---|---|---|---|
| | | | | | Oil and surfactant flow rate (µL/h) | Gel flow rate (µL/h) |
| 70 | 40 | 40 | 2.5 | 3 | 40 | 70 |
| 150 | 150 | 100 | 3 to 4 | 7 | 550 | 750 |
| | | 300 | 3 to 4 | 7 | 200 | 750 |
| 300 | 100 | 40 | 3 | 3 | 200 | 70 |
| | | 300 | 3 | 7 | 150 | 700 | cells escaping from their traps. In one example, the microfluidic trapping array can have a 150 μm tap diameter, 300 μm trap height, and 100 μm tall microfluidic layer.

On-Chip Viability Study

Live and dead staining were carried out after nine days of on-chip cell culture using the live stain Calcium AM (Life Technologies) and the dead stain Ethidium homodimer-1 (EthD-1, Life Technologies) of concentrations 3.75 μM and 4.5 μM respectively in ECB. Live and dead stain mixtures were flowed through the device at a rate of 350 μL/h for 1 hour and 45 minutes using a Harvard syringe pump. The device was incubating at 37° C. during the whole time of stain mixture flow. Finally, cellular fluorescence was visualized using a Leica DMi8 inverted microscope outfitted with a FITC filter cube, rhodamine filter, and brightfield applications at 5× objective. Digital images were acquired using the Flash 4.0 high-speed camera (Hamamatsu) with a fixed exposure time of 15 ms for the FITC filter (green, live cells), 100 ms for the rhodamine filter (red, dead cells), and 20 ms for brightfield. This on-chip viability study shows that most of the cells are living with few dead (FIGS. 20A-20E). This indicates that the device is cell-culture compatible, and with correct protocols, it can be used for rapid and high throughput spheroid generation.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A tunable cell culture material comprising a hydrogel, wherein the hydrogel is a product of a reaction between a thiol and an acrylate;
   wherein the thiol comprises ethoxylated trimethylolpropane tri (3-mercapto-propionate) (ETTMP), and the acrylate comprises poly(ethylene glycol) diacrylate (PEGDA); and
   when the hydrogel weight percent is about 8.5 and the molar ratio is about 1.0, the gelation time is about 150 minutes;
   when the hydrogel weight percent is about 8.5 and the molar ratio is about 1.05, the gelation time is about 40 minutes;
   when the hydrogel weight percent is about 9 and the molar ratio is about 1.0, the gelation time is about 80 minutes;
   when the hydrogel weight percent is about 9 and the molar ratio is about 1.05, the gelation time is about 30 minutes;
   when the hydrogel weight percent is about 9.5 and the molar ratio is about 1.0, the gelation time is about 30 minutes; and
   when the hydrogel weight percent is about 9.5 and the molar ratio is about 1.05, the gelation time is about 25 minutes.

2. A tunable cell culture material of claim 1, wherein the reaction is a base-catalyzed Michael addition occurring at a pH of about 7.6 to 8.2.

3. The tunable cell culture material of claim 1, further comprising a liquid medium;
   wherein the liquid medium comprises an extracellular buffer (ECB) comprising the following components: HEPES, NaCl, KCl, $MgCl_2 \cdot 6H_2O$, $CaCl_2 \cdot 2H_2O$, and glucose.

4. The tunable cell culture material of claim 3, wherein the hydrogel comprises from about 8.5 to about 10.5 wt % of the material.

5. The tunable cell culture material of claim 4, wherein the thiol and acrylate are present in a molar ratio of about 1 to about 1.05 thiol groups per acrylate group.

6. The tunable cell culture material of claim 5, wherein:
   when the molar ratio is about 1.0, the material has a swelling ratio of about 2.5 to about 4.0 after 4 hours; and
   when the molar ratio is about 1.05, the material has a swelling ratio of about 4 to about 7 after 24 hours.

7. The tunable cell culture material of claim 3, wherein:
   a relative weight of the material decreases to no greater than one millionth of an original weight of the material in pH 8.05 DMEM in about 60 to about 200 hours; and
   a relative weight of the material decreases no greater than one millionth of an original weight of the material in pH 7.9 phosphate buffered saline in about 100 to about 425 hours.

8. A method for culturing cells, the method comprising:
   a. providing a tunable cell culture material comprising a hydrogel according to claim 1;
   b. seeding the cells in the hydrogel to form a seeded hydrogel;
   c. contacting the hydrogel with a culture medium; and
   d. allowing the cells to grow for a period of from about 4 days to about 17 days.

9. The method of claim 8, wherein about 95 to about 97% of cells seeded in the hydrogel are viable after 17 days.

10. The method of claim 8, wherein the culture medium comprises HEPES, NaCl, KCl, $MgCl_2 \cdot 6H_2O$, $CaCl_2 \cdot 2H_2O$, and glucose.

11. The method of claim 8, wherein the seeded hydrogel is provided to a microfluidic droplet-generating device in an aqueous phase and the seeded hydrogel gelates inside the microfluidic droplet-generating device.

12. The method of claim 8, wherein the cells form spheroids having a diameter of about 100 μm to about 300 μm.

13. The method of claim 8, further comprising introducing the seeded hydrogel to a microfluidic device after step b, such that the contacting with the culture medium occurs inside the microfluidic device.

14. A tunable cell culture material comprising:
   a hydrogel and a liquid medium;
      wherein the hydrogel is a product of a reaction between a thiol and an acrylate;
      wherein the thiol comprises ethoxylated trimethylolpropane tri (3-mercapto-propionate) (ETTMP), and the acrylate comprises poly(ethylene glycol) diacrylate (PEGDA); and
      wherein the liquid medium comprises an extracellular buffer (ECB) comprising the following components: HEPES, NaCl, KCl, $MgCl_2 \cdot 6H_2O$, $CaCl_2 \cdot 2H_2O$, and glucose.

15. The tunable cell culture material of claim 14, wherein:
   a relative weight of the material decreases to no greater than one millionth of an original weight of the material in pH 8.05 DMEM in about 60 to about 200 hours; and a relative weight of the material decreases no greater than one millionth of an original weight of the material in pH 7.9 phosphate buffered saline in about 100 to about 425 hours.

16. The tunable cell culture material of claim 14, wherein the hydrogel comprises from about 8.5 to about 10.5 wt % of the material.

17. The tunable cell culture material of claim 16, wherein the thiol and acrylate are present in a molar ratio of about 1 to about 1.05 thiol groups per acrylate group.

18. The tunable cell culture material of claim 17, wherein:
when the molar ratio is about 1.0, the material has a swelling ratio of about 2.5 to about 4.0 after 4 hours; and
when the molar ratio is about 1.05, the material has a swelling ratio of about 4 to about 7 after 24 hours.

\* \* \* \* \*